Figure 1:
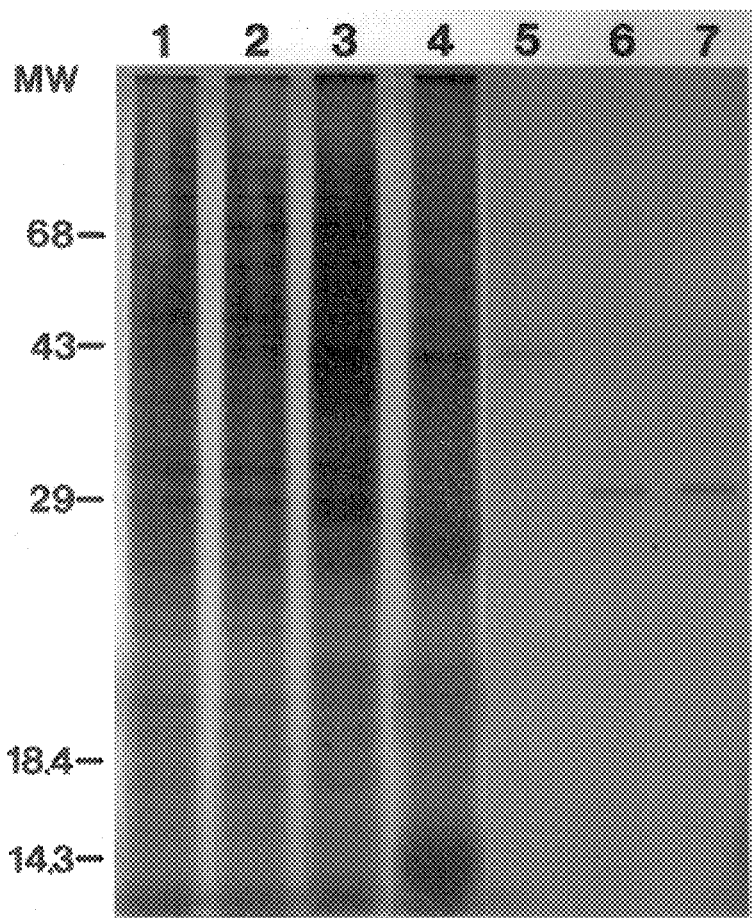

United States Patent [19]
St.Leger et al.

[11] Patent Number: 5,962,765
[45] Date of Patent: *Oct. 5, 1999

[54] MOLECULAR CLONING OF A COMPLIMENTARY DNA SEQUENCE ENCODING A CUTICLE DEGRADING PROTEASE PRODUCED BY ENTOMOPATHOGENIC FUNGI

[75] Inventors: Raymond J. St.Leger; Donald W. Roberts; Richard C. Staples, all of Ithaca, N.Y.

[73] Assignee: Boyce Thompson Institute for Plant Research, Inc., Ithaca, N.Y.

[*] Notice: This patent is subject to a terminal disclaimer.

[21] Appl. No.: 08/382,505

[22] Filed: Feb. 2, 1995

Related U.S. Application Data

[63] Continuation-in-part of application No. 07/739,645, Aug. 8, 1991.

[51] Int. Cl.$^6$ ............... C12N 5/14; C12N 1/15; C12N 1/21; A01N 63/04
[52] U.S. Cl. ............ 800/298; 435/6; 435/69.1; 435/252.3; 435/254.11; 435/320.1; 424/93.2; 424/93.5; 536/23.2
[58] Field of Search .................. 435/69.1, 218, 435/219, 240.2, 252.3, 320.1, 223, 6, 68.1, 254.11; 530/350, 351; 536/22.1, 23.1, 23.2, 23.74; 800/298; 424/93.2, 93.5

[56] References Cited

U.S. PATENT DOCUMENTS

| | | |
|---|---|---|
| 4,987,077 | 1/1991 | Charnley et al. ............ 435/223 |
| 5,266,317 | 11/1993 | Tomalski et al. ............ 424/93 |

OTHER PUBLICATIONS

Gupta, A.S. et al, 1993, Increased Resistanct To Oxidative Stress In Transgenic Plants That Overexpress chloroplastic Cu/Zu Superoxide dismutase, Proc. Natl. Acad. Sci, USA, vol. 90, pp. 1629–1633.
Clare, B.G. et al, 1990, Agrobacterium in Plant Disease, Biological Disease Control and Plant Genetic Engineering, Sci. Progress, 74: 1–13.
Binns, A.N. et al, 1988, Cell Biology of Agrobacterium Infection and Transformation of Plants, Ann. Rev. Microbiol., 42: 575–606.
Betzel, C. et al, Active-site geometry of proteinase K, FEBS Letters vol. 197, pp. 105–114, (1986).
Carter, P. et al, Dissecting the catalytic triad of a serine protease, Nature, vol. 332 (1988) pp. 564–568.
Charnley, A.K. et al, The Role of Cuticle-Degrading Enzymes in Fungal Pathogenesis in Insects, Plenum Press, pp. 267–286, (1991).
Davidow, L.S. et al, Cloning and Sequencing of the Alkaline Etracellular Protease Gene of Yarrowia lipolytica, Jnl. of Bact., (Oct. 1987), pp. 4621–4629.
Deane, S. et al, Nucleotide sequence of the Vibrio alginolytieus calcium-dependent, detergent-resistant alkaline serine exoprotease A, Gene, 76 (1989) pp. 281–288.
Egeling, W. et al, Proteinase K from Tritirachium album Limber, Eur.J. Biochem, 47, (1974) pp. 91–97.
Flurkey, W.H. et al, In Vitro Translation of Cutinase mRNA: Evidence for a Precursor Form of an Extracellular Fungal Enzyme, Archi. of Bioch and Biophysis, (1981) vol. 2112, pp. 154–161.
Goettel, M.S. et al, Ultrastructural Localization of a Cuticle-degrading Protease Produced by the Entromopathogenic Fungus Metarhizium anisopliae during Penetration of Host (Manduca sexta) Cuticle, Jnl of Gen Microb. (1989) 135, 2233–2239.
Goettel, M.S. et al., Pathogenicity and growth of Metarhizium anisopliae stably transformed by benomyl resistance, Curr Genet (1990) 17: 129–132.
Gunkel, F.A. et al, Proteinase K from Tritirachium album Limber, Eur. J. Biochem. (1989) 179, 185–194.
Heale, J.B. et al, Prospects for Strain Improvement in Entomopathogenic Fungi, Pestic. Sci. (1989) 26: 79–92.
Heale, J.B., The Potential Impact of fungal genetics and molecular biology on biological control, with particular reference to entomopathogens, pp. 2121–234, (1991).
Jany, K. et al, Amino acid sequence of proteinase K from the mond Tritirachium album Limer, Elsevier Sci. Publ., (Apr. 1986) vol. 199:139–144.

(List continued on next page.)

*Primary Examiner*—Kawai Lau
*Attorney, Agent, or Firm*—Brown, Pinnisi & Michaels, PC

[57] ABSTRACT

We have studied the regulation of the extracellular chymoelastase protease (Pr1) of *Metarhizium anisopliae*, an enzyme involved in the penetration of insect cuticle by Metarhizium and other entomopathogenic fungi. We report here the isolation and characterization of a Pr1 cDNA clone with a full length insert. Pr1 is synthesized as a large precursor (40.3 kDa) containing a signal peptide and a propeptide and the mature protein is predicted to have a relative molecular mass of 28.6 kDa. The primary structure of Pr1 shares extensive homology (30–60%) with enzymes of the subtilisin subclass of the serine endopeptidases and the serine, histidine and aspartyl components of the active site in subtilisins are preserved. The genes coding for chymoelastase or slightly altered versions thereof, can be used to transform various organisms (i.e. fungi, viruses, plants, bacteria, etc.) such that the transformed organisms are capable of producing chymoelastase in recoverable quantities. Fragments and derviatives of a DNA sequence coding for a chymoelastase could be used to code for a polypeptide having an activity which can: a) bind to insect cuticle; b) enhance signal processing of proteins; c) hydrolyse polypepetides; d) suppress protease expression; or e) be used as a probe to identify homologous genes in organisms. While chymoelastases and Pr1 have been previously isolated, new and novel uses for chymoelastase are disclosed, wherein the chymoelastase is used to selectively degrade protein in the presence of non-protein polymers. A new insecticide insecticide is disclosed which comprises a recombinant virus, microorganism, cell, plant or fungi infects, is eaten by or otherwise taken up by, an insect and expresses the enzyme Pr1 within said insect such that Pr1 activates a prophenoloxidase system within said insect.

14 Claims, 11 Drawing Sheets 3

OTHER PUBLICATIONS

Kaneko, R. et al, Molecular Cloning of athe Structural Gene for Alkaline Elastase YaB, a New Subtilisin Produced by an Alkalophilic Bacillus Strain, Jnl of Bacter., (Sep. 1989) pp. 5232–5236.

Hepburn, H.F., Structure of the Integument, Pergamon Press, vol. 3, pp. 1–58, (1991).

Kessler, E. et al, Synthesis, Processing, and Transport of Pseudomonas aeruginosa Elastase, Jnl. of Bacter., (Nov. 1988) pp. 5241–5247.

Gurr, S.J. et al, The structure and organization of nuclear genes of filamentous fungi, Soc. Gen Microbiology, vol. 22, (1987) pp. 93–139.

Kramer, K.J. et al, Insect Cuticle Structure and Metabolism, American Chemical Soc., (1987) Chaper 12, pp. 160–185.

Kraut, J., Serine Proteases: Structure and Mechanism of Catalysis, Ann. Rev. Biochem. (1977) 46:331–358.

Laemmli, U.K., Cleavage of Structural Proteins during the Assembly of the Head of Bacteriophage T4, Nature, vol. 227, (1970) pp. 680–685.

DeLorenzo, G. et al, Induction of Extracellular Polygalacturonase and Its mRNA in the Phytopathogenic Fungus Fusarium moniliforme, Jnl. Gen. Microbiology, (1987) 133: 3365–3373.

Lovett, J.S., The Molocular Biology of Fungal Development, vol. 2, Macmillar Publ. Co., pp, 64–100, (1991).

Maniatis, T. et al, Molecular Cloning–A Laboratory Manual, (1982), Cold Spring Harbor Laboratory, pp. 194–195.

Matsuzawa, H. et al, Purification and characterization of aqualysin I (a thermophilic alkaline serine protease) produced by Thermus aquatics YT–1, Eur. J. Biochem. (1988) 171: 441–447.

McCoy, C.W. et al, Dntomogenous Fungi, vol V., Part A., CRC Press, Inc., pp. 151–236, (1991).

Moehle, C.M. et al, Protease B. of the Tysosomelike Vacuole of the Yeast Sccharomyces cerevisiae is homologous to the Subtilisin Family of Serine Proteases, Mole and Cell Biol., (Dec. 1987) pp. 4390–4399.

Moehle, C.M. et al, Processing Pathway for Protease B. of Saccharomyces cerevisiae, Jnl of Cell Biol., vol. 108, (Feb. 1989) pp. 309–324.

Roberts, D.W. et al, Use of Pathogens in Insect Control, vol. II, CRC Press, Inc., pp. 243–278, (1991).

Roberts, D.W., World Picture of Biological Control of Isnects by Fungi, Mem. Inst. Oswaldo Cruz, Rio de Janeiro, Bol. 85, (1989) pp. 89–99.

Robets, D.W et al, Entomogenous Fungi, Biol. of Conidial Fung, vol. 2, (1981), pp. 201–235.

Sambrook, J. et al, Identification of cDNA Clones of Interest, Cold Spring Harbor Lab. Press, pp. 8.46–8.86, (1991).

Samal, B.B. et al, Cloning and expression of the gene encoding a novel proteinase from Tritirachium album Limer, (1989), Gene. 85:329–333.

Sive, H.L. et al, A simple subtractive hybridization technique employing photoactivatable biotin and phenol extraction, Nucl Acid Res., vol.16 (1988).

Tatsumi, H. et al, A full length cDNA clone for th alkaline protease from Aspergillus oryzae: Strctural analysis and expression in Saccharomyces cerevisiae, Mol. Gen. Genet (1989) 219:33–38.

St.Leger, R.J., (1990), The role of cuticle–degrading enzymens in fungal pathogenesis of insects. In Vth Intern. Colloquium on Invertebrate Pathology and Microbial Control, Preceedings held Adelaide, Australia, pp. 308–312.

St.Leger, R.J. et al, (1991), Kinetics of the digestion of insect cuticles by a protease (Pr1) from Metarhizium anisopliae, J. Invertebr. Pathol. 57: 146–147.

St.Leger, R.J. et al, (1991), Characterization of chitinolytic enzymes produced by the entomopathogen *Metarhizium anisopliae*., J. Invertebr. Pathol. 58: 415–426.

St.Leger, R.J. et al, (1991), Prepenetration events during infection of host cuticle by Metarhizium anisopliae, J. Invert. Pathol., 58:168–179.

St.Leger, R.J. et al, (1992), Fungi for the biocontrol of insects: Tools and trends. In Molecular Biol. of Filamentous Fungs, pp. 45–63.

Staples, R.C. et al, (1989), Strategies for genetic engineering of fungal entomopathogens. In Biothechnology, Biological Pesticides and Novel Plant–Pest Resistance for Insect Pest Management, Cornell Univ., Ithaca, NY pp. 44–48, (1991).

Josky, L. et al, (1995), Cloning of a cuticle–degrading protease form the entomopathogenic fungus, Beauveria bissiana, FEMS Micro Letters, pp. 211–218.

Terada, I. et al, Unique precursor Structure of an Extracellular Protease, Aqualysin I, with $NH_2$— and COOH–terminal Pro–seqences and Its Processing in *Escherichia coli,* Jnl. of Biol Chem., (1990), pp. 6576–6581.

Watson, M.E., Compilation of Published signal sequences, (1984), vol. 12, pp. 5145–5164.

Wells, J.A. et al, Cloning sequencing, and secretion of Bacillus amyloliquefaciens subtilisin in Bacillus subtilis, Nucl. AcidRes., (1983), vol. 11, pp. 7911–7925.

Woloshuk, C.P. et al, Mechanism by which contact with plant cuticle triggers cutinase gene expression in the spores of Fusarium solani f. sp. pisi., Pro. Natl. Acad. Sci., (Mar. 1986), Vo. 83, pp. 1704–1708.

Williams, J.G. et al, Characterization and Transcription Analysis of a Cloned Sequence Derived froma Major Developmentally Regulated mRNA of D. discoideum, Cell, vol. 17, (Aug. 1979), pp. 903–913.

Wright, C.S. et al, Structure of Subtilisin BPN' at 2–5 A Resolution, Nature, (1969), vol. 221, pp.235–242.

Yoder, O.G. et al, Prospects for Development of Molecular Technology for Fungal Insect Pathogens, Academic Press, (1987). pp. 197–218.

Thompson, W.F., Phytochrome control of RNA levels in developing pea and mung–gean leaves, planta (1983) 1158: 487–500.

St.Leger, R.J. et al, Cuticle–Degrading Enzymes of Entomopathogenic Fungi: Mechanisms of Interaction between Pathogen Enzymes and Insect Cuticle, Jnl of Invert. Path, (1986) 47: 295–302.

St. Leger, R.J., Intergument as a Barrier to Microbial Infections, Boyce Thompson Institute, Cornell Univ. USA, 24 pages, (1991).

St. Leger, R.J. et al, Cuticle–degrading enzymes of Entomopathogenic fungi: Regulation of production of chitinolytic enzymes., J. gen. Microbiol. (1986) 132: 1509–1517.

St. Leger, R.J. et al, Cuticle–degrading enzymes of entomopathogenic fungi: Synthesis in culture on cuticle, (1986) J. Invert. Pathol. 48:85–95.

St.Leger, R.J. et al, Cuticle–degrading enzymes of entomopathoginic fungi: Cuticle degrading in vitro by enzymes from entomopathogens, J. Invertebr, Pathol. (1986), 47:167–177.

St. Leger, R.J. et al, Distribution of chymoelastases and trypsin–like enzymes in five species of entomopathogenic deuteromycetes, (1987) Arch. Biochem. Biophys. 258: 123–131.

St. Leger, R.J., et al, Production of cuticle–degrading enzymes by the entomopathogen Metarhiziuman isopliae during infection of cuticles from Calliphora vomitoria and Manduca sexta, (1987), J. Gen Microbiol. 133:1371–1382.

St. Leger, R.J. et al, Characterization of cuticle–degrading proteases produced by the enatomopathogen Metarhizium anisopliae, (1987), Arch. Biochem. Biophys, 253: 221–232.

St. Leger, R.J. et al, Regulation of production of proteolytic enzymes by the entomopathogenic fungus Metarhizium anisopliae, (1988), Arch. Microbiol. 150: 413–416.

St.Leger, R.J. et al, Role of extracellular chymoelastase in the virulence of Metarhizium anisopliae for Manduca sexta, (1988), J. Invertebr. Pathol. 52:285–293.

St. Leger, R.J. et al, Novel GTP–binding proteins in plasma membranes of the fungus Metarhizium anisopliae, (1989), Biochem. Biophys. Res. Comm. 164:562–566.

St.Leger, R.J. et al, Calcium and calmodulin–mediated protein synthesis and protein phosphorylation during germination, growth and protease production by Metarhizium anisopliae, (1989), J. Gen Microbiol. 135: 2141–2154.

St.Leger, R.J. et al, Synthesis of proteins including a cuticle–degrading protease during differentiation of the entomopathogenic fungus Metarhizium anisopliae, (1989), Exp. Mycol. 13:253–262.

St.Leger, R.J. et al, Production in vitro of appressoria by the entomopathogenic fungus Metarhizium anisoplia, (1989), Exp. Mycol. 13: 274–288.

St.Leger, R.J. et al, Changes in translatable mRNA species associated with nutrient deprivation and protease synthesis in Metarhizium anisopliae, (1991), J. Gen. Microbiol. 137:807–815.

St.Leger, R.J. et al, Kinetics of the Digestion of Insect Cuticles by a Protease (Pr1) from Metarhizium anispoliae, (1991) J. of Invert Pathol., 57:146–147.

Loros, J.J. et al, (1991) Neurospora crassa Clock–Controlled Genes Are REgulated at the Level of Transportation, Mole and Cell Biol, vol. 11: 558–563.

Paietta, J.V., (1989) Molecular Cloning and Regulatory Analysis of the Arylsulfatase Structural Gene of Neurospora crassa, Mole and Cell Biol, vol. 9: 3630–3637.

Bidochka, M.J. et al, Differentiation of species and strains of entomopathogenic fungi by random amplification of polymorphic DNA (RAPD), (1991), Curr. Genet. 25: 107–113.

Hajek, A. et al, Interactions of entomopathogenic fungi and insect hosts leading to eqpizootic development, (1994), Annual Review of Entomology, 39: 293–323.

St.Leger, R.J. et al, Second messenger involvement in differentiation of the entomopathogenic fungus Metarhizium anisopliae, (1990), J. Gen. Microbiol. 136:1779–1789.

St.Leger, R.J. et al, Protein kinases in the entomopathogenic fungus Metarhizium anisopliae, (1990) J. Gen. Microbiol. 136:1401–1411.

St.Leger, R.J. et al, Electrophoretic detection of multiple protein kinases in the entomopathogenic fungus Metarhizium anisopliae, (1990), Arch. Microbiol. 154: 518–520.

St.Leger, R.J. et al, Molecular cloning and regulatory analysis of the cuticle–degrading protease structural gene from the entomopathogenic fungus Metarhizium anisopliae, (1992), Eur. J. Biochem. 204:991–1001.

St.Leger, R.J. et al, Cloning and regulatory analysis of ssgA: A gene encoding a hydrophobin–like protein from the entomopathogenic fungus, Metarhizium anisopliae, (1992), Gene 120: 119–124.

St.Leger, R.J. et al, Analysis of aminopeptidase and dipeptidylpeptidase from the entomopathogenic fungus Metarhizium anisopliae, (1993), J. Gen. Microbiol. 1139: 237–243.

St.Leger, R.J. et al, Isoforms of the cuticle–degrading Pr1 protease and production of a metalloproteinase by Metarhizium anisopliae, (1994), Arch. Biochem. Biophys., 313:1–7.

St.Leger, R.J. et al, Charcterization of a novel carboxypeptidase produced by the entomopathogenic fungus Metarhizium anispliae, (1994), Arch. Biochem. Biophys., 3114:392–398.

Roberts, D.W. et al, Entomopathogenic fungi: recent basic and applied research, Proc. Internat. Enference on Biopesticides, Theory and Practice, Czechoslovakian Academy of Sciences, (1990), pp. 11–30.

Roberts, D.W. et al, (1992), Entomopathogenic fungi as bioinsecticides. In Frontiers in Industrial Mycology, Chapman and Hall, pp. 144–159.

Glover "Principles of cloning DNA"*Gene cloning* (1984) pp. 1–19.

Bernier, L. et al. "Technology for molecular cloning of virulence genes in the fungal entomopathogen Metarhizium anisopliae" BCPC Monograph (1989), vol. 43, p. 269, Abtract.

Alberts, B. et al. Molecular Biology of the Cell, Second Edition. New York, Garland Publishing, Inc., 1989, pp. 258–265.

Fig. 7a

```
CGCGGGCCGCATTCCATCAAATCAACCTCGGTTCTGCCCAACATTCTCGGTCTTTGGTCCGTACTAGAATTTGCAATC
                               -100                  -80                                       →

MET His Leu Ser Ala Leu Leu Thr Leu Pro Ala Val Leu Ala Ala Pro Ala Thr Ile
ATG CAT CTG TCT GCT CTT CTC ACT CTT CCA GCC GTT CTG GCT GCC CCT GCC ACT ATT

Gly Arg Arg Ala Glu Pro Leu Phe Pro Thr Pro Gln Ala Glu Ser Ile Ile Ala Asp
GGC CGG CGC GCT GAG CCA CTT CCT CTC ACT CCT CAG GCT GAG AGC ATT ATT GCC GAC
                      -60

Lys Tyr Ile Val Lys Phe Asp Ile Ala Arg Ile Ala Thr Asp Thr Val Ser
AAG TAT ATT GTC AAG TTC GAT ATT GCC CGT ATC GCT ACC GAT ACG GTG AGC
        -40

Ala Leu Thr Ser Lys Ala Asp Phe Val Tyr Glu His Gly Phe His Ala Gly Ser
GCT CTT ACC TCC AAA GCC GAC TTC GTT TAC GAG CAC TTC CAT GCA GGC TCC
                -20

Leu Thr Lys Glu Glu Leu Lys MET Leu Arg Glu His Pro Gly Val Asp Phe Ile Glu Lys
CTC ACC AAG GAG GAG CTG AAG ATG CTT CGT GAG CAC CCC GGT GTC GAT TTC ATT GAG AAG
                                  -1 | +1

Asp Ala Val MET Arg Ile Ser Gly Ile Thr Glu Gln Ser Gly Ala Pro Trp Gly Leu Gly
GAC GCT GTG ATG CGT ATC AGC GGC ATC ACT GAG CAG AGC GGT GCT CCC TGG GGT CTT GGG
                            ↑

Arg Ile Ser His Arg Ser Lys Gly Ser Thr Thr Tyr Arg Tyr Asp Asp Ser Ala Gly Gln
CGC ATC TCT CAC CGC AGT AAG GGA AGC ACC ACC TAT CGC TAC GAT GAT AGT GCT GGT CAG

Gly Thr Cys Val Tyr Ile Ile Thr Gly Ile Ala Ser His Pro Glu Phe Gly Gly
GGT ACT TGC GTA TAT ATC ACT GGT ATT GAG GCC TCC CAC CCC GAG TTT GAG GGT
                                                    20

Arg Ala Thr Phe Leu Lys Ser Phe Ile Ser Lys Thr Asp Gly His Gly His Gly
CGC GCC ACT TTT CTT AAG AGC TTC ATC AGC AAG ACT GAT GGC CAC GGG
                40

Thr His Cys Ala Gly Thr Ile Gly Ser Lys Thr Tyr Gly Val Ala Lys Lys Leu
ACT CAC TGC GCT GGT ACC ATT GGT AGC AAG ACC TAC GGT GTT GCC AAA AAG CTC
                60

Tyr Gly Val Lys Val Leu Asp Asn Gln Gly Ser Gly Ser Tyr Ser Gly Ile Ile Ser Gly
TAT GGT GTC AAG GTT CTT GAC AAC CAG GGC AGT GGT TCC TAC TCC GGT ATC ATC AGT GGC
                80

MET Asp Tyr Val Ala Gln Asp Ser Lys Thr Arg Gly Cys Pro Asn Gly Ala Ile Ala Ser
ATG GAC TAC GTT GCA CAG GAC TCC AAG ACC CGC GGC TGC CCC AAC GGC GCC ATT GCT TCC
                                100
```

Fig. 7

| Fig. 7A |
| Fig. 7B |

Fig. 7b

```
       MET Ser Leu Gly Gly Gly Tyr Ser Ala Ser Val Asn Gln Gly Ala Ala Leu Val Asn
       ATG AGC CTG GGA GGT GGT TAC TCG GCG TCC GTC AAC CAA GGT GCT GCT TTG GTC AAT
                               120                                            140
       Ser Gly Val Phe Leu Ala Val Ala Gly Asn Asp Arg Asn Asp Ala Gln Asn Thr Ser
       TCT GGT GTC TTC CTT GCC GTC GCC GGT AAC GAT AAC CGG GAT GCC CAG AAC ACC TCT
       Pro Ala Ser Glu Pro Ser Ala Cys Thr Val Gly Ala Ser Ala Glu Asn Asp Ser Arg Ser
       CCC GCT TCC GAG CCT TCT GCC TGC ACT GTT GGT GCC TCT GCG GAA AAT GAC AGC TCT
                                   160                                        180
       Ser Phe Ser Asn Tyr Gly Arg Val Val Asp Ile Phe Ala Pro Gly Ser Asn Val Leu Ser
       TCC TTC TCC AAC TAC GGC AGA GTT GTC GAT ATT TTC GCT CCT GGT AGC AAT GTT CTT TCC
                                           200
       Thr Trp Ile Val Gly Arg Thr Asn Ser Ile Ser Gly Thr Ser MET Ala Thr Pro His Ile
       ACC TGG ATT GTT GGC CGC ACA AAC TCC ATC TCT GGT ACC TCC ATG GCT ACT CCC CAT ATT
                                       220
       Ala Gly Leu Ala Ala Tyr Leu Ser Ala Leu Gln Gly Lys Thr Thr Pro Ala Ala Leu Cys
       GCC GGT CTG GCC TAC CTC AGT GCG CTC CAA GGC AAG ACT ACC CCT GCC GCT CTT TGC
                                               240
       Lys Lys Ile Gln Asp Thr Ala Thr Lys Asn Val Leu Thr Gly Val Pro Ser Gly Thr Val
       AAG AAG ATC CAG GAC ACT GCT ACC AAG AAC GTG CTC ACC GGT GTT CCC TCT GGC ACT GTC
                                                   260

Asn Tyr leu Ala Tyr Asn Gly Ala ***
       AAC TAC CTT GCC TAC AAC GGT GCCTAAAATTCTTAACTTGAGCAAGGGGGAACCCTTCAGTGAAGACGGCGAT
                                   280

TGGTTGGTTGTATATTTGAGATAATTTCCAACGCTCGAATCCCCCCCAAAGGTATATATTTATATATTCTATATTTCTTCACC

AGTACATTATGATGAACATGACCTTTCCCAATATAAGATGTCTTTGCAGCAGAAGGAAATGAAGATGTTATCGGGCGTG

TAGCTCAGAGTGCAGAAGTTGAGCTACTAGGGAATAAATCTAGGAGAGTTTATGGCCAAAAAAAAAAAAAAGCGGCCGCG
```

Fig. 7

| Fig. 7A |
|---------|
| Fig. 7B |

FIG. 8

```
PR1         .....MHLSALLTLLPAVLAAPATIGRRAEPAPLFTPQAESIIADKYIVK  -62
             |  ||  || |||  | |||    |  |  |||       |   | ||||||
Proteinase K .....MRLSVLLSLLPLALGAPA.VEQRSEAAPLIEARGE.MVANKYIVK
             |  |  |   |      |         | ||      |      ||||
SUBT $B     MRGKKVWISLLFAL.ALIFTMAFGSTSSAQAA......GKSNGEKKYIVG PR1         FKDDIARIATDDTVSALTSKADFVYEHA..FHGFAGSLTKEELKMLREHP  -14
            ||   |  | |         | ||       |  |  |  || ||   ||  ||
Proteinase K FKEGSALSALDAAMEKISGKPDHVYKNV..FSGFAATLDENMVRVLRAHP
            ||            ||   |  |        |||  |  || |
SUBT $B     FKQTMSTMSAAKKKDVISEKGGKVQKQFKYVDAASATLNEKAVKELKKDP PR1         GVDFIEKDAVMRISGITEQSGAPWGLGRISHRSKGSTTYRYDDSAGQGTC   36
            |  || |||   |         |  |||||| |||   || ||  ||||||
Proteinase K DVEYIEQDAVVTINA..AQTNAPWGLARISSTSPGTSTYYYDESAGQGSC
            | | | |   |   T     |          |   |       |
SUBT $B     SVAYVEEDHVAHAYA....QSVPYGVSQIKAPALHSQGY.....TGSNVK PR1         VYIIDTGIEASHPEF..EGRATFLKSFISGQNTDGHGHGTHCAGTIGS..   82
            || |||||||||||||  ||||   |       || |||||||||||| ||
Proteinase K YYVIDTGIEASHPEF..EGRAQMVKTYYS.SRDGNGHGTHCAGTVGS..
            |  ||  ||   |||      | |        |  | | | | | |||||
SUBT $B     VAVIDSGIDSSHPDLKVAGGASMVPS.ETNPFQDNNSHGTHVAGTVAALN PR1         ...KTYGVAKKAKLYGVKVLDNQGSGSYSGIISGMDYVAQDSKTRGCPNG  129
               |||||||  | ||||||||| ||| ||| || ||| ||  |  || |
Proteinase K ...RTYGVAKKTQLFGVKVLDDNGSGQYSTIIAGMDFVASDKNNRNCPKG
               |||  |  |||||||| ||| |||   |     |   |  |
SUBT $B     NSIGVLGVAPSASLYAVKVLGADGSGQYSWIINGIEWAIANNMD......

PR1         AIASMSLGG.GYSASVNQGAAALVNSGVFLAVAAGNDNRDAQNTS...PA  175
            || ||||||  ||| |||  |||  |||  ||||||||| | || |   ||
Proteinase K VVASLSLGG.GYSSSVNSAAARLQSSGVMVAVAAGNNNADARNYS...PA
             |  ||||||    |    |  |   |       |||  |  ||       |
SUBT $B     .VINMSLGGPSGSAALKAAVDKAVASGVVVVAAAGNEGTSGSSSTVGYPG PR1         SEPSACTVGASAENDSRSSFSNYGRVVDIFAPGSNVLSTWIVGRTNSISG  225
            ||||  |||||       | ||||||||| | |  || |||||  |  ||||
Proteinase K SEPSVCTVGASDRYDRRSSFSNYGSVLDIFGPGTSILSTWIGGSTRSISG
            |||   |||  |    ||  |      |   ||   ||  ||         |
SUBT $B     KYPSVIAVGAVDSSNQRASFSSVGPELDVMAPGVSIQSTLPGNKYGAYNG PR1         TSMATPHIAGLAAYLSALQGKTTPAALCKKIQDTATK.NVLTGVPSGTVN  274
            |||||||  ||||||| |  ||||      | | |  |  |||| ||  |||
Proteinase K TSMATPHVAGLAAYLMTL.GKTAASACRYIADTANK.GDLSNIPFGTVN
            |||||||||||| |                   |  |        |   |
SUBT $B     TSMASPHVAGAAALILSKHPNWTNTQVRSSLENTTTKLGDSFYYGKGLIN PR1         YLAYNGA..  281
            ||||
Proteinase K LLAYNNYQA
            |
SUBT $B     VQAAAQ...
```

MOLECULAR CLONING OF A COMPLIMENTARY DNA SEQUENCE ENCODING A CUTICLE DEGRADING PROTEASE PRODUCED BY ENTOMOPATHOGENIC FUNGI

CROSS REFERENCE TO RELATED APPLICATIONS

This is a continuation-in-part of co-pending application Ser. No. 07/739,645, filed Aug. 8, 1991, entitled "MOLECULAR CLONING OF A COMPLIMENTARY DNA SEQUENCE ENCODING A CUTICLE DEGRADING PROTEASE PRODUCED BY ENTOMOPATHOGENIC FUNGI."

ACKNOWLEDGMENT OF GOVERNMENT SUPPORT

This invention was made with government support under Grant No. 89-37263-4463 and Grant No. 92-37307-7791, awarded by the USDA. The government has certain rights in the invention.

FIELD OF THE INVENTION

The present invention relates to the isolation of translatable mRNA and the molecular cloning of a complimentary DNA sequence encoding for a cuticle degrading protease produced by entomopathogenic fungi, and more particularly relates to the isolation of translatable mRNA and the molecular cloning of a complimentary DNA sequence encoding for the cuticle-degrading protease, chymoelastase, produced by the entomopathogenic fungus *Metarhizium anisopliae*.

BACKGROUND OF THE INVENTION

Proteins form the major component of insect cuticle to which they impart structural rigidity. The cuticle is an effective barrier to most microbes but entomopathogenic fungi can breach it using extracellular proteases. Consequently, fungal pathogens are the only biological means of controlling aphids and other sap-sucking insects which would not naturally ingest viruses or bacteria; and they are important for coleopteran control since viral and bacterial diseases are unknown for most beetle pests.

"World Picture of Biological Control of Insects by Fungi", Mem. Inst. Oswaldo Cruz, Rio de Janeiro, Vol. 84, Supl. III, 89–100, 1989, by Donald W. Roberts, joint inventor, is an overview of the role of entomopathegenic fungi and is incorporated herein by reference. Virtually all insect orders are susceptible to fungal diseases. Fungi are particularly important in the control of pests which feed by sucking plant juices, because these insects have no means of ingesting pathogens. There are approximately 700 species of entomopathogenic fungi in almost 100 genera (see table 1 of Roberts, 1989).

Entomopathogenic fungi frequently decimate insect populations in spectacular epizootics and are already used for the biological control of some pest species, as discussed in "Use of pathogens in insect control" by D. W. Roberts et al, In: Handbook of Pest Management in Agriculture, 2nd ed., Vol. 2 (Pimentel, D., ed.), CRC Press, Boca Raton, Fla. pp. 243–278, 1991, incorporated herein by reference. Nevertheless, the considerable potential of entomopathogenic fungi for pest control has never been realized, largely because so little is known about the genetic and molecular basis of fungal pathogenesis in insects, as discussed in "Prospects for development of molecular technology for development of molecular technology for fungal insect pathogens", by Yoder et al, In: Biotechnology in Invertebrate Pathology and Cell Culture. Academic Press, NY. pp. 197–218, 1987; and in "The potential impact of fungal genetics and molecular biology on biological control, with particular reference to entomopathogens" by J. B. Heale, In: Fungi in Biological Control Systems (M. Burge, ed.) Manchester University Press, Manchester pp. 211–234, 1988; both incorporated herein by reference. Such knowledge is urgently needed to allow the genetic engineering of fungi for use as biological control agents.

Current widely-publicized problems with synthetic chemical insecticides have given rise to a sense of urgency in the development of biological control agents as supplements or alternatives to these chemicals. Although widely used in some less-developed nations, entomopathogenic fungi have only recently assumed importance in United States agriculture and household entomology. This is in spite of the fact that entomopathogenic fungi are key regulatory factors in pest insect populations, are considered very promising biological control agents and provide the only practical means of biological control of insects which feed by sucking plant or animal juices, and for the many coleopteran pests which have no known viral or bacterial diseases. The imperfect fungus, *Metarhizium anisopliae*, was registered by the U.S. EPA in 1993 for cockroach control, and registration packages for use of *Beauveria bassiana*, another imperfect fungus, in agriculture have been submitted. *Verticillium lecanii* is registered in Europe, and there is interest in it in the USA, particularly for whitefly control. Any consideration of the suitability of a microorganism for commercial purposes inevitably leads to the possibility of improving its performance. This is particularly true for traditional biopesticides (viruses, bacteria, and fungi) as their performance is commonly perceived to be poor compared with chemical pesticides. However, registration requests to date have been for naturally-occurring fungi obtained by standard selection procedures and improved as pathogenic agents by developing the technologies required for optimizing production and stability of the inoculum. Improvements have also been attempted through parasexual crossing and protoplast fusion (Heale et al, 1989).

Genetic engineering using transformation and gene cloning for pathogenicity traits that are regulated by single genes or gene clusters provides the most targeted and flexible approach to dissect, and eventually alter, the physiology of entomopathogenic fungi without the cotransfer of possibly undesirable linked characteristics. The use of genetically engineered microorganisms can also produce combinations of traits that are not readily identified in nature, even if they exist somewhere. Of greatest importance, genetic engineering allows transfer of pathogenicity genes between species, genera, and even kingdoms. Entomopathogenic fungi represent an unconsidered, and therefore untapped, reservoir of pesticidal genes for the production of advanced engineered pesticides; an important consideration, given that the lack of "useful" pesticidal genes for transfer has been a major constraint in the implementation of biotechnology in crop protection (Gatehouse et al., 1992).

One of the most promising candidates for widespread commercial use is the deuteromycete, *Metarhizium anisopliae* ("Entomogenous Fungi" by McCoy et al, 1988 In: CRC Handbook of Natural Pesticides, Vol. 5: Microbial Insecticides Part A, Entomogenous Protozoa and Fungi (Ignoffo, C. M., ed.) CRC Press, Boca Raton, Fla. p. 151, incorporated herein by reference.). The process by which this pathogen colonizes an insect host has been examined in order to develop, through genetic manipulation, fungi which are appropriate for the control of specific insect pests. The chymoelastase proteases produced by *M. anisopliae* and other pathogenic fungi currently provide the best understood model of a fungal determinant of entomopathogenicity ("The role of cuticle-degrading enzymes in fungal pathogenesis in insects" by Charnley, A. K. and St. Leger, R. J, 1991, In: The Fungal Spore and Disease Initiation in Plants and Animals (Cole, G. T. and Hoch, H. C., eds.). Plenum Press, NY. pp. 267–286, incorporated herein by reference.).

The term "chymoelastase" is used hereinabove to describe an elastolytic enzyme with a primary specificity for amino acids with large hydrophobic side groups. An elastolytic enzyme, or elastase, is a functional term describing an enzyme capable of solubilizing elastin, usually with a primary specificity for amino acids with small hydrophobic side chains, e.g. alanine. By contrast, a chymoelastase with elastolytic activity has optimum activity against typical substrates for chymotrypsins, e.g. phenylalanine. Chymoelastase is a good general purpose stain remover because of its broad range of specificity for protein substrates. Pr1 has similar substrate specificity to subtilisin-like enzymes and subtilisin-like enzymes is a broad category of enzymes recognized by those skilled in the art. The primary chymoelastase produced by *M. anisopliae* believed to be primarily responsible for the invasion through insect cuticle has been named Pr1 and the terms "chymoelastase" and "Pr1" are used interchangeably hereinabove.

The importance of Pr1 during Metarhizium infection processes was suggested, firstly, by its considerable ability to degrade cuticle, which is attributed (at least in part) to the structural importance and assessibility of cuticular proteins ("Characterization of cuticle-degrading proteases produced by the entomopathogen *Metarhizium anisopliae*" by R. J. St. Leger, *Arch. Biochem. Biophys.* 253, 221–232, 1987a, incorporated herein by reference.); and, secondly, by its high level at the site of penetration before and coincident with hydrolysis of cuticle proteins ("Ultrastructural localization of a cuticle-degrading protease produced by the entomopathogenic fungus *Metarhizium anisopliae* during penetration of host (*Manduca sexta*) cuticle", by M. S. Goettel et al, *J. Gen. Microbiol.* 135, 2233–2239, 1989; "Production of cuticle-degrading enzymes by the entomopathogen *Metarhizium anisopliae* during infection of cuticles from *Calliphora vomituria* and *Manduca sexta*", by R. J. St. Leger et al, *J. Gen. Microbiol.* 133, 1371–1382, 1987b; and "Synthesis of proteins including a cuticle-degrading protease during differentiation of the entomopathogenic fungus *Metarhizium anisopliae*" by R. J. St. Leger et al, *Exp. Mycol.* 13, 253–262, 1989a; all incorporated herein by reference. It has also been demonstrated that antisera against Metarhizium Pr1 or specific inhibitors of Pr1 block penetration of host cuticles and reduce infection indicating that the regulation of expression of the Pr1 gene may determine the capacity of the fungus to cause disease ("Role of extracellular chymoelastase in the virulence of *Metarhizium anisopliae* for *Manduca sexta*" by R. J. St. Leger et al, *J. Invertebr. Pathol.* 52, 285–293, 1988a, incorporated herein by reference).

The purified Pr1 has been characterized for substrate specificity and inhibition by typical serine protease inhibitors (St. Leger et al., 1987b). Utilization of pathogen enzymes, particularly Pr1, has assisted investigators to understand how the cuticle is degraded naturally, and it is predicted that further characterization will enable manipulation of enzyme levels using chemical and biotechnological procedures for the purpose of insect control ("Insect cuticle structure and metabolism", by Kramer et al., In: Biotechnology for Crop Protection (Hedin, P. A., Menn, J. J. and Hollingworth, R. M., eds.) American Chemical Society, Washington pp. 160–183, 1988, incorporated by reference). For example, the characterization of genes for anticuticular enzymes is an important step towards engineering vectors for introduction of these genes into other microbes and plants.

Potentially, specialization for a pathogenic lifestyle may operate by way of regulatory controls which allow expression of genes under conditions in which similar genes are not expressed in non-pathogens. Previously, it was demonstrated that antisera against Metarhizium Pr1 or specific inhibitors of Pr1 block penetration of host cuticles and reduce infection indicating that the level of active Pr1 may determine the capacity of the fungus to cause disease (St. Leger et al., 1988a). Production of the enzyme without differentiation of infection structures can occur rapidly by nutrient deprivation alone ("Regulation of production of proteolytic enzymes by the entomopathogenic fungus *Metarhizium anisopliae*", by R. J. St. Leger et al, *Archives Microbiology* 150: 413–416, 1988b, incorporated herein by reference.) making Metarhizium an amenable system for the study of the molecular controls of protein synthesis.

SUMMARY OF THE INVENTION

It is, therefore, an object of the present invention to provide a method of obtaining translatable mRNA from a variety of species of fungi capable of producing chymoelastase.

It is a further object of the present invention to provide isolated translatable mRNA coding for chymoelastase.

It is a further object of the present invention to provide a cDNA clone for chymoelastase.

It is a further object of the present invention to provide a cDNA clone with the deduced amino acid sequence for chymoelastase.

It is a further object of the present invention to provide a transformed organism by inserting a transformation vector including a cDNA clone for chymoelastase.

It is a further object of the present invention to provide new and novel uses for chymoelastase in selectively degrading protein in the presence of non-protein polymers.

One of the discoveries of the present invention, is that translatable mRNA coding for chymoelastase can be isolated from *Metarhizium anisopliae*. Chymoelastase transcript was isolated from fungus capable of producing a chymoelastase, by: a) growing the fungus on nutrient rich media; b) transferring the fungus to nutrient poor media; c) after growth on the nutrient poor media, extracting mRNA from the fungus; and d) isolating said chymoelastase transcript from said extracted mRNA. Isolates of other entomopathogenic fungi (*Verticillium lecanii, Beauveria bassiana, Topypocladium niveum* and *Paecilomyces farinosus*) produced chymoelastases during nutrient deprivation, demonstrating that this method has widespread application in entomopathogenic fungi. Some of the teachings of the present invention relating to the isolation and analysis of translatable mRNA coding for cuticle degrading proteases in Metarhizium were presented in "Changes in translatable mRNA species associated with nutrient deprivation and protease synthesis in *Metarhizium anisopliae*" by R. J. St. Leger et al, *J. Gen. Microbiol.* 137, 807–815, 1991.

A further discovery of the present invention is the cloning of the cuticle-degrading protease (Pr1) gene of *Metarhizium*

*anisopliae*. A cDNA library was constructed from mycelia deprived of nutrients for three hours. The library was differentially screened by using cDNA probes from rapidly growing mycelia and nutrient deprived mycelia. Southern blot analysis showed that some of the clones hybridized to an oligonucleotide probe synthesized from a sequence of amino acid residues at the N-terminus of the purified Pr1 protein.

A further discovery of the present invention is the nucleotide sequence for this cDNA and the deduced amino acid sequence for Pr1. Further analysis of the cDNA has provided insights into the regulation and enzymology of chymoelastase. The cDNA sequence revealed that Pr1 is synthesized as a large precursor (40.3 kDa) containing a signal peptide and a propeptide and the mature protein is predicted to have a relative molecular mass of 28.6 kDa. The primary structure of Pr1 shares extensive homology (30–60%) with enzymes of the subtilisin subclass of the serine endopeptidases and the serine, histidine and aspartyl components of the active site in subtilisins are preserved. Proteinase K demonstrated the closest sequence homology with Pr1 (61%) but Pr1 was two-fold more effective than Proteinase K at degrading isolated cuticles of *Manduca sexta* and 33-fold more effective at degrading structural proteins bound to cuticle by covalent bonds. The more positive surface charge of the Pr1 molecule, as compared with proteinase K, may facilitate electrostatic binding to cuticle proteins which is a prerequisite for activity. The Pr1 cDNA clone and a cDNA clone of a coordinately regulated gene ('starvation-specific gene') were used to demonstrate transcriptional control of expression during nutrient deprivation and during formation of infection structures.

By utilizing the information provided hereinabove and by following the teachings of the present invention it is possible to engineer variously altered genes for chymoelastase to enhance binding potential, substrate specificity, etc. The genes coding for chymoelastase or slightly altered versions thereof, can be used to transform various organisms (i.e. fungi, viruses, plants, bacteria, etc.) such that the transformed organisms are capable of producing chymoelastase in recoverable quantities. Fragments and derivatives of a DNA sequence coding for a chymoelastase could be used to code for a polypeptide having an activity which can: a) bind to insect cuticle; b) enhance signal processing of proteins; c) hydrolyse polypeptides; d) suppress protease expression; or e) be used as a probe to identify homologous genes in organisms.

While chymoelastases and Pr1 have been previously isolated, new and novel uses for chymoelastase are disclosed, wherein the chymoelastase is used to selectively degrade protein in the presence of non-protein polymers.

Until recently, recombinant DNA techniques had no application in a strain improvement program for entomopathogenic fungi because there was no information available as to the nature of the genes that control either pathogenesis or specificity. We have developed molecular biology methods to elucidate pathogenic processes in Metarhizium and have cloned a gene (Pr1) which is expressed when the fungus is induced by starvation stress to alter its saprobic growth habit, develop a specialized infection structure-the appressorium-and attack its insect host. This is the first pathogenicity-related genes to be cloned from an entomopathogenic fungus.

Our work illustrates how the isolation and in situ manipulation of such genes allow the biochemical role of their encoded products to be defined and has led to the production of transgenic fungi with improved pathogenic characteristics. We have improved *M. Anisopliae* by genetic engineering. Furthermore, we teach how to utilize the Pr1 gene to improve baculoviruses and plants for use in insect biocontrol. Within this objective, we teach a recombinant *Autographa californica* polyhedrosis virus strains expressing fungal proteins which are toxic when injected into insects and may be expected to have a similar effect when produced by the baculovirus; e.g., the *M. anisopliae* hydrophobin and Pr1 protease. Genetic engineering of crops for insect resistance using genes from entomopathogenic fungi will produce transgenic plants expressing fungal proteins which are toxic per os or are feeding inhibitors.

These and other objects, features and advantages of the present invention should become apparent from the following description when taken in conjunction with the accompanying drawings.

BRIEF DESCRIPTION OF THE DRAWINGS

FIG. 1. Protein coding capacities of poly($A^+$)RNA from Metarhizium during production of Pr1.

FIG. 2. Changes in the mRNA population during nutrient deprivation.

FIG. 3. Detection of starvation specific RNA species and Pr1 using dot blots.

FIG. 4. Detection of starvation specific RNA species and Pr1 during differentiation of appressoria.

FIG. 5. Pulse chase analysis on the accumulation of Pr1 and Pr1 precursors by Metarhizium in 3 hour minimal media culture.

FIG. 6. Southern blot analysis of restricted chromosomal DNA from *M. anisopliae.*

FIG. 7. Nucleotide sequence of the Pr1 cDNA clone lPr1 and its translation into amino acid sequence from an ATG start codon to a termination codon (TAA).

FIG. 8. Homology between pro-Pr1 and the subtilisin family enzymes proteinase K and subtilisin BPN'.

FIG. 9. Pile up of nine microbial proteases.

FIG. 10. Southern blot analysis of restricted chromosomal DNA from *M. anisopliae* (ME1), *A. flavus* and *V. lecanii.*

FIG. 11. Computer-aided secondary structure analysis of the predicted pro-Pr1 peptide.

FIG. 12. Regulation of synthesis of Pr1 and ssg. genes at the level of transcription during nutrient deprivation.

FIG. 13. Changes in the mRNA population during nutrient deprivation.

FIG. 14. Detection of Pr1 and ssg. mRNA during differentiation of appressoria.

FIG. 15. The activities of Pr1 and proteinase K against proteins extracted from cuticles of *Manduca sexta.*

DETAILED DESCRIPTION OF THE PREFERRED EMBODIMENT

For the purposes of promoting an understanding of the teachings of the present invention, references will now be made to the embodiments described hereinabove and in the drawings and specific language will be used to describe these embodiments. It will nevertheless be understood that no limitation of the scope of the invention is thereby intended, alterations and further applications of the teachings of the present invention as illustrated and described hereinabove is anticipated by those skilled in this art.

Abbreviations: —CN, no carbon or nitrogen source; EDTA, ethylenediaminetetraacetic acid; NAG, N-acetylglucosamine; PAGE, polyacrylamide gel electrophoresis; PMSF, phenyl methyl sulfonyl fluoride; SDB, Sabouraud dextrose broth; SDS, sodium dodecyl sulfate; SSC, sodium chloride-sodium citrate buffer; TLCK, tosyl-lysine-chloroketone; YEM, yeast extract media.

Isolates

Isolates of Verticillium lecanii (ARSEF 313), Paecilomyces farinosus (ARSEF 1508), Tolypocladium niveum (ARSEF 616) and Beauveria bassiana (ARSEF 252) were obtained from the USDA-ARS culture collection, Cornell University, Ithaca, N.Y., USA. The isolates were grown and maintained on Sabouraud dextrose agar (SDA) at 23° C.(V. lecanii), 25° C.(B. bassiana), 27.5° C.(other isolates), and stored at 4° C. The isolates of M. anisopliae var. anisopliae [ME1 (ex. Curculio caryae, Curculionidae Coleopt.) 23 (ex. Conoderus vespertinus, Elateridae: Coleopt.) (ex.Austracris guttulosa, Acrididae: Orthopt.), 817 (ex. Otiorhynchus sulcatus, Curculionidae: Coleopt.) and 2951 (ex. Isoptera)] were used as well. Pathogenic isolates of Verticillium lecanii (313, Aphid pathogen "Vertelac" produced by Tate & Lyle, Research and Development, Reading, UK), Aspergillus flavus (1002, es. Bombyx mori, Bonbycidae: Lepidopt.), Zoophthora (=Erynia) radicans (1019, ex. Empoasca fabae, Cicadellidae: Homopt.) were obtained from the USDA-ARS culture collection, Cornell University, Ithaca, N.Y., USA. While the specific isolates listed above were used in the discovery of the teachings of the present invention, the procedures taught hereinabove can be used to obtain translatable mRNA or cDNA coding for chymoelastase from a variety of entomopathogenic fungi and the teachings of the present invention are not meant to be limited to the specific isolates listed hereinabove.

tion (Table 1). In response these fungi produced activities against the Pr1 substrate (Suc-(Ala)2-Pro-Phe-pNA (Table 1). Pr1 activity vs. succinyl-(alanine)2-proline-phenylalanine-p-nitroanilide (Suc-(Ala)2-Pro-Phe-pNA) was assayed as described by St. Leger et al. (1987b). Clean samples of cuticle from 3-day-old fifth instar Manduca sexta larvae were prepared as described previously (St. Leger et al., 1988b). As reported previously for Metarhizium (St. Leger et al., 1988a), enzyme levels were frequently enhanced in cultures supplied with Manduca cuticle or other insoluble protein or non-protein (cellulose) polymers at levels insufficient to produce catabolite repression. However, in each case production of protease was repressed in SDB or when N-acetylglucosamine (1%) was added to medium containing cuticle, showing that repression overrides the enhancing effect of polymeric substrates. The production of extracellular proteases by starved mycelia apparently required de novo RNA synthesis as activities were reduced by the transcriptional inhibitor actinomycin D (Table 1).

Further studies conducted on Metarhizium demonstrated that the source of fungal inocula influenced protease (Pr1) release. Fungal inocula from 3 day cultures grown on 2% N-acetylglucosamine/basal salts cultures ("Cuticle-degrading enzymes of entomopathogenic fungi: Synthesis in culture on cuticle", by R. J. St. Leger et al, Journal of Invertebrate Pathology 48: 85–95, 1986a, incorporated herein by reference) a relatively poor growth medium (growth rate 1.5±0.31 mg dry wt. ml$^{-1}$ day) but sufficient to repress Pr1 synthesis, allowed appearance of Pr1 within 1 hour of transfer to minimal media (—CN, 0.01% $KH_2PO_4$, 0.005% $MgSO_4$). By contrast Pr1 activity was only apparent

TABLE 1

Protease production by five species of entomopathogenic fungi 8 hour after transfer of growing mycelium to nutrient rich or nutrient-limiting conditions.

| Medium | M. Anisopliase[a] | V. Lecaniia | B. Bassiana[a] | P. Farinosusa | T. Niveuma |
|---|---|---|---|---|---|
| —CN[b] | 32.7 ± 4.53[c] | 24.7 ± 3.94 | 20.9 ± 3.57 | 6.3 ± 0.84 | 21.6 ± 2.6 |
| —CN + Manduca cuticle (0.5%) | 75.2 ± 6.82 | 36.2 ± 3.13 | 30.3 ± 2.85 | 10.41 ± 1.42 | 29.4 ± 1 |
| —CN + chitin (0.5%) | 51.1 ± 4.31 | 32.8 ± 4.30 | 34.1 ± 4.31 | 7.9 ± 0.38 | 31.8 ± 3.7 |
| —CN + cellulosed (0.5%) | 44.3 ± 5.62 | 28.6 ± 2.62 | 29.5 ± 2.65 | 9.19 ± 0.83 | 38.6 ± 2.4 |
| —CN + Manduca cuticle (0.5%) + NAG (1%) | 0.2 ± 0.01 | 2.27 ± 0.13 | 0 | 0 | 3.4 ± 0.54 |
| —CN + Actinomycin D (100 mg ml − 1) | 8.6 ± 0.81 | 4.38 ± 0.44 | 7.23 ± 0.23 | 0 | 7.38 ± 0.85 |
| SDB | 0 | 0 | 0 | 0 | 0 |

[a]Except for V. lecanii (23° C.) and B. bassiana (25° C.) isolates were incubated at 27° C.
[b]—CN; minimal media (0.01% $KH_2PO_4$, 0.005% $MgSO_4$) without carbon or nitrogen source.
[c]Protease activity was measured spectrophotometrically with Suc-(Ala2-Pro-Phe-pNA as the substrate. Results represent mean protease activity (nmol nitroanilide ml − 1 min − 1) for 3 replicates ± SD. The results are representative of two similar experiments.
[d]Insoluble crystalline cellulose.

Production of Pr1 During Nutrient Deprivation

Mycelia of five species of entomopathogenic fungi, growing rapidly in SDB cultures, were transferred to media in which growth was limited by carbon and nitrogen deprivation after 3 hour using inocula from 32 hour SDB cultures (growth rate 3.97±0.53 mg dry wt. ml$^{-1}$ day) or 3 d SDB cultures (4.5±0.43 mg dry wt. ml$^{-1}$ day). Pr1 activity 4 hour post-transfer from 3 d SDB cultures or 4 hour post-transfer from 3 d NAG cultures was 13.64±1.8 nmoles pNA ml$^{-1}$ min$^{-1}$ and 45.42±3.6 nmoles pNA ml$^{-1}$ min$^{-1}$ respectively. Pr1 was not detected in Metarhizium growth media following transfer of cultures from SDB to fresh SDB, or after a heat shock treatment (55° C., 5 min). Thus the production of Pr1 is not a component of a stereotyped response to stress but part of an adjustment to altered growth conditions.

Quantitative Changes in the mRNA Production

The complement of mRNA sequences present during differentiation have been examined in two ways. First, the cell-free translation products of poly(A$^+$)RNA were analyzed at different times during nutrient deprivation. Second, subtraction hybridization experiments were performed between poly(A$^+$)RNA's isolated at different times, and their complementary DNA's in order to analyze gross changes in the mRNA population during starvation. Changes in mRNA sequences during starvation-induced synthesis of chymoelastase were investigated by comparing poly(A$^+$) RNAs and their complementary DNA in rapidly growing or nutrient-deprived cultures of Metarhizium. Hybrid-selected translation revealed that three novel polypeptides were produced rapidly (<1 h) during nutrient deprivation; the most intensely translated species was identified as the primary translation product of Pr1.

At various intervals during Pr1 production in nutrient deprived media (without carbon and nitrogen source), poly(A$^+$)RNA was extracted and their protein coding capacities were assessed in a cell free rabbit reticulocyte translation system.

Extraction procedures for RNA. Total RNA was extracted from small fungal samples using guanidine HCl. Infection structures (appressoria) were induced by germinating conidia in YEM (0.0125%) on glass petri dishes as described previously (St. Leger et al., 1989a). RNA was extracted after pouring off the YEM supernatant and adding 2.5 ml of homogenizing buffer (7.5 M guanidine HCl, 0.1% sarcosyl, 0.1 M 2—mercaptoethanol, 10 mM EDTA, 50 mM sodium citrate, pH 7). Adherent germlings were scraped off and the buffer was then transferred sequentially to five other dishes. The mycelia from 30 dishes were pooled and homogenized by mixing in a vortex for 5 min with acid washed glass beads (1 g) (<0.3 mm diam.). Following centrifugation, supernatants were heated at 65° C. for 5 min and extracted by phenol/chloroform extraction and the RNA was ethanol precipitated ("Molecular cloning: a laboratory manual", pp. 194–195, by T. Maniatis et al, Cold Spring Harbor, N.Y.: Cold Spring Harbor Laboratory, 1982, incorporated by reference). After dissolving in water, some samples were treated with RNase A (overnight) or DNase I (1 h) at 0.1 mg ml$^{-1}$ in the presence of 10 mM MgCl,. Treated extracts were processed for dot blot analysis as described below.

Washed conidia (400 mg) harvested from 10-day-old SDA cultures (St. Leger et al., 1989a), acid washed glass beads (1,200 mg) (<0.3 mm diam.) and liquid nitrogen were placed in a 50 ml centrifuge tube and vortexed for 5 periods of 5 min each, with renewal of liquid nitrogen as needed. Rapidly, before the contents of the tube were thawed, the fractured conidia and glass were suspended in 5 ml of homogenization buffer. All subsequent steps were as described for germlings.

Preparation and translation of poly(A)RNA (mRNA). Poly(A)RNA was isolated from finely comminuted frozen mycelium by phenol/chloroform extraction, precipitation of the total RNA with ethanol, and isolating the poly(A)RNA using oligo(dt) chromatography (Maniatis et al., 1982). Poly(A)RNA was dissolved in sterile water, aliquoted and stored at −70° C. until used. Poly(A)RNA was translated in a rabbit reticulocyte cell-free translation system. Normally 1 µg poly(A)RNA was translated in 40 µl of solution containing 35 µl of nuclease treated rabbit reticulocyte lysate (Promega), 1 unit/µl of RNasin (Promega), a mixture of unlabelled amino-acids minus methionine (25 µM final concentration), and 1.5/µCi/µl of [$^{35}$S] methionine (Amersham) for 1 hour at 30° C.

Immunoprecipitations. Translation products were analyzed by immunoprecipitation as described by Anderson, D. J. and Blobel, G. (1983) in "Immunoprecipitation of proteins from cell-free translations", Methods in Enzymology 96: 111–120, incorporated by reference, with modifications. Samples (10 µl) of the translation mixture were added to 20 vol. of immunoprecipitation buffer (1% skimmed milk, 1.1% Triton X- 100, 100 mM Tris-HCl, pH 7.8, 100 mM NaCl, 10 mM Na, EDTA, 1 mM PMSF, 0.1 mM aprotinin, 0.02 mM TLCK and 0.02 mM leupeptin) and incubated sequentially for 1 hour each with 10 µl of pre-immune serum and 30 µl of 1:1 suspension of protein A-sepharose (Sigma) and immunoprecipitation buffer at 4° C. The samples were spun for 2 min in a microcentrifuge and the supernatants incubated sequentially for 1 hour each with 1 µl of rabbit polyclonal antisera specific for Pr1 (St. Leger et al., 1989a) and 30 µl of the protein A-sepharose suspension. The sepharose beads were washed extensively in the immunoprecipitation buffer, minus the skimmed milk, followed by a wash in the similar buffer, minus detergents. Pr1 was eluted from the beads by boiling in SDS sample buffer ("Cleavage of structural proteins during the assembly of the head of bacteriophage T4", by U. K. Laemmli, Nature, London 227: 680–684, 1970, incorporated herein by reference) for 5 min and analyzed by SDS-PAGE and autoradiography (St. Leger et al., 1989a). The same procedure was used to conduct immunoprecipitation experiments on labelled mycelial proteins. Ten microliter samples of cell lysate in lysis buffer or growth media were added to 20 vol. of immunoprecipitation buffer before proceeding as above.

Immunoblotting. Proteins, denatured by boiling for 10 min, were placed in 1 µl aliquots onto nitrocellulose pre-wetted with 10 mM Tris buffered (pH 7.4) saline (150 mM NaCl). Blots probed with anti-Pr1 serum were developed with alkaline phosphatase coupled antibody to rabbit IgG according to the ProtoBlot Western blot AP system technical manual (Promega) except that 1% skimmed milk powder was used as blocking agent.

FIG. 1 shows protein coding capacities of poly(A)RNA from Metarhizium during production of Pr1. Poly(A)RNA was extracted from mycelia incubated in minimal media for (1) 0 hour (mycelia taken directly from 1% NAG/basal salts media); (2) 0.5 h; (3) 1 h; (4) 7 hour and translated in the presence of [$^{35}$S]-methionine (5, 6, 7) translation products from poly(A) RNA from 1 hour minimal media cultures were processed and immunoprecipitated with anti-Pr1-bodies (5) and compared with immunoprecipitated samples of active Pr1 from culture filtrates of 2 hour minimal media cultures (6) and 2 hour 0.5% chitin/basal salts media cultures (7).

Figure 2:
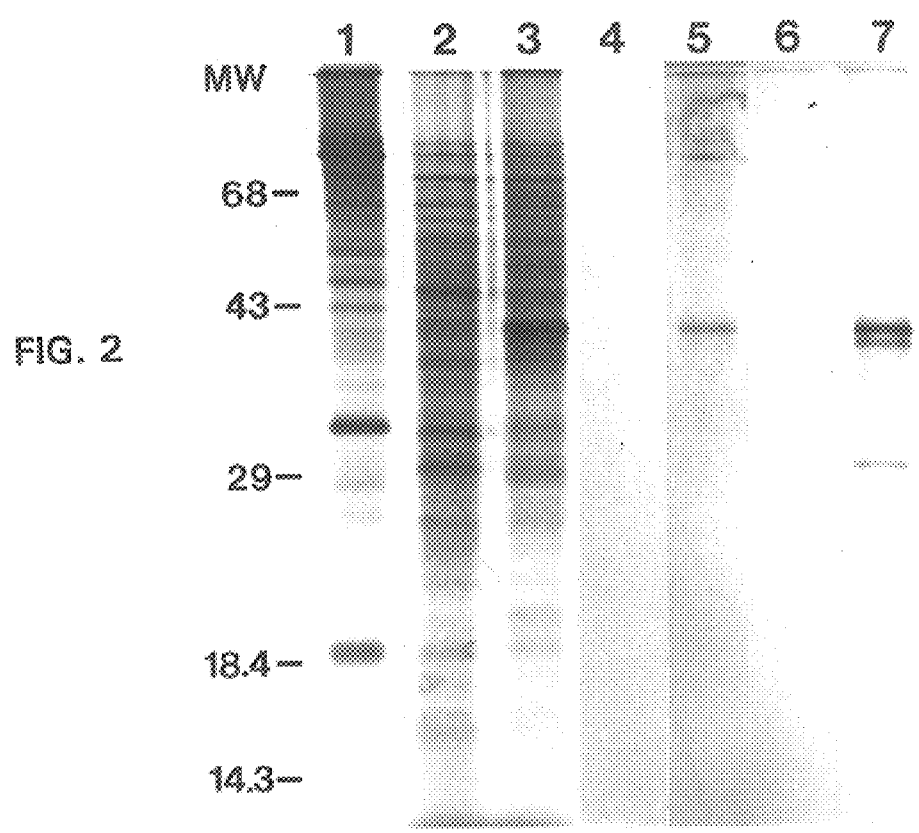

The patterns observed with NAG medium and nutrient deprived medium were very similar until 60 min post-transfer when there was a considerable induction of mRNA for a 41 kDa protein (FIG. 1). The quality of poly(A)RNA had deteriorated in mycelia harvested after several hours in nutrient deprived conditions. Some of the bands became faint, broad or indistinct. However the transcript for the 41 kDa protein apparently retained its integrity better than most other transcripts (FIG. 1, lane 4), suggesting maintained synthesis and/or that it is a peculiarly stable species. Its protein product comigrated on Na Dod $SO_4$/polyacrylamide gels with the single protein (41 kDa) precipitated from translation mixtures by anti-Pr1-serum, and which was likewise absent in mycelia grown in nutrient rich medium (FIG. 2). Pr1 (5 $\mu$g) added to the translation mixture before addition of the antibody effectively competed with the 41 kDa translation product, strongly suggesting that this protein is immunologically similar to the mature Pr1 from Metarhizium in spite of the 11 kDa difference in molecular mass (FIG. 1).

FIG. 2 shows changes in the mRNA population during nutrient deprivation. Protein coding capacities of poly(A) RNA isolated from Metarhizium from NAG cultures (lane 2) and from cultures transferred from minimal NAG cultures media for 2 hour (lane 3). Immunoprecipitation of translation products from 3 d NAG cultures (lane 4) and 1 hour minimal media (lanes 5 and 6) cultures. Translation products were processed and immunoprecipitated with anti-Pr1-serum as described above with the exception of the sample in lane 6 which was immunoprecipitated after adding 5 $\mu$g of Pr1. Poly(A)RNA isolated from 1 hour minimal media cultures was hybridized to diazotized paper discs bearing cDNA which had been constructed from the same poly(A) RNA and subsequently subtracted with poly(A)RNA isolated from 3 d NAG cultures. RNA was eluted from the discs and translated (lane 7). Lane 1 shows translation products from Brome Mosaic Virus RNA used as a positive control of the translation system.

To clarify further changes in the mRNA population, subsequent analysis was carried out on mRNA enriched for transcripts present only in the nutrient-deprived mycelia. FIG. 2 (lane 7) shows a typical autofluorogram of the in vitro synthesized polypeptides obtained from hybrid selected mRNA. By this method it was possible to detect the de novo appearance of three major translatable mRNA species for polypeptides of Mw 41, 40.2 and 29.8 kDa. Anti-Pr1 serum selectively precipitated only the 41 kDa species indicating that the 40.2 and 29.8 kDa proteins are immunologically unrelated to Pr1.

Synthesis of subtracted complementary DNA (cDNA) probes. Large scale synthesis of single stranded cDNA was performed using 30 $\mu$g of purified poly(A)RNA from 2 hour minimal media cultures (0.01% $KH_2$, $PO_4$, 0.005% $MgSO_4$, without carbon or nitrogen source) as template and using random primers as described in "*Molecular Cloning: A Laboratory Manual*, 2nd edition Vol. 2, Sect. 8, by J. Sambrook et al, Cold Spring Harbor, N.Y.: Cold Spring Harbor Laboratory, 1989, incorporated herein by reference. Radiolabelled cDNAs for probes were synthesized by replacing the unlabelled dCTP with [$\alpha$-$^{32}$P]dCTP (3000 Ci mmol: 1 Ci=37 GBq; New England Nuclear) at 2 Ci ml$^{-1}$. After incubation at 37° C. for 1 h, the reaction was stopped by the addition of 20 $\mu$l of 0.2 M EDTA, and the RNA was hydrolyzed by the addition of 25 $\mu$l of 1 M NaOH and incubation for 30 min at 70° C. After neutralization the unincorporated label was removed by centrifugal Sephadex G-50 chromatography (Maniatis et al., 1982). Single stranded radiolabelled cDNA (13 $\mu$g) was subtracted, to obtain unique sequences, with 100 $\mu$g of poly(A)RNA from 3 d SDB cultures using a hybridization technique employing photoactivatable biotin and phenol extraction essentially by the method of Sive, H. L. and St. John, T. (1988) "A simple subtractive hybridization technique employing photoactivatable biotin and phenol extraction", *Nucleic acids research* 16: 10937, incorporated herein by reference, except that the volume of all components in the reaction were increased by a factor of 5 to match the amount of cDNA. Three similar cycles of hybridization were performed to drive the subtraction hybridization to completion.

Analysis of the subtracted cDNA was by hybridization/ selection ("Isolation of specific RNA's using DNA covalently linked to diamobenyloxymethyl cellulose on paper", by M. L. Goldberg et al, *Methods in Enzymology* 68: 207–220, 1979, incorporated herein by reference.). The subtracted cDNA was immobilized onto a 0.5 cm$^2$ disc of freshly diazotized (diazobenzyloxymethyl, DBM) Whatman 540 paper ("Characterization and transcription analysis of a cloned sequence derived from a major developmentally regulated mRNA of *D. discoideum*", by J. G. Williams et al, *Cell* 17: 903–913, 1979, incorporated herein by reference). The disc was hybridized for 6 hour at 37° C. with 0.15 tig of Poly(A)RNA from 1 hour minimal media cultures in 50/II of buffer (50% formamide, 0.8 M NaCl, 0.2% SDS, 2 mM EDTA, 20 mM PIPES at pH 6.4). The disc was washed at 37° C. four times for 20 min each with 200 ml of 20 mM NaCl, 8 mM Trisodium citrate, 50% formamide and 0.2% SDS and twice in 200 ml of 2×SSC. RNA was eluted from the filters by shaking in 100 $\mu$l of extraction buffer (20 mM PIPES pH 6.4, 0.5% SDS, 1 mM EDTA and 90% formamide). The eluates from 10 similar hybridization cycles using the same disc (which had been recycled through an alkaloid elution step between hybridizations) were combined and diluted with 2 vol. of water, wheatgerm tRNA was added to 20 $\mu$g ml$^{-1}$ and the RNA was ethanol precipitated. Samples were reprecipitated from ethanol and washed in 70% ethanol. After dissolving in water, samples were translated using rabbit reticulocyte lysate.

RNA dot blots. To further analyze whether starvation-induced mRNA species involved transcription, dot blot analysis of total RNA was conducted using the subtraction [$^{32}$P] cDNA probe. Dot blots were performed by the procedure of W. F. Thompson et al, "Phytochrome control of RNA levels in developing peas and mung bean leaves", *Planta* 158: 487–500 (1983), incorporated herein by reference. RNA, denatured with 6% formaldehyde in 20 mM Na phosphate, pH 6.8, at 55° C. was placed in 2 $\mu$l aliquots on pre-wetted (water, then 2×SSC) nitrocellulose membranes (BA85 Schleicher and Schnell). Following baking at 80° C. under vacuum, hybridization was conducted with the subtracted [$^{32}$P] cDNA probe at 42° C. for 15 hour in 50% formamide, 3×SSC, I×Renhardt's medium, 200 $\mu$g ml$^{-1}$ yeast RNA and 20 $\mu$g ml$^{-1}$ denatured salmon sperm RNA. Blots were washed sequentially in 2×SSC (2×10 min, 23° C.), 0.1×SSC plus 0.1% SDS (3×20 min, 50° C.) and rinsed rapidly three times in 0.1×SSC plus 0.1% SDS at 23° C., and three times in 0.1% SSC before analysis by autoradiography.

Figure 3:
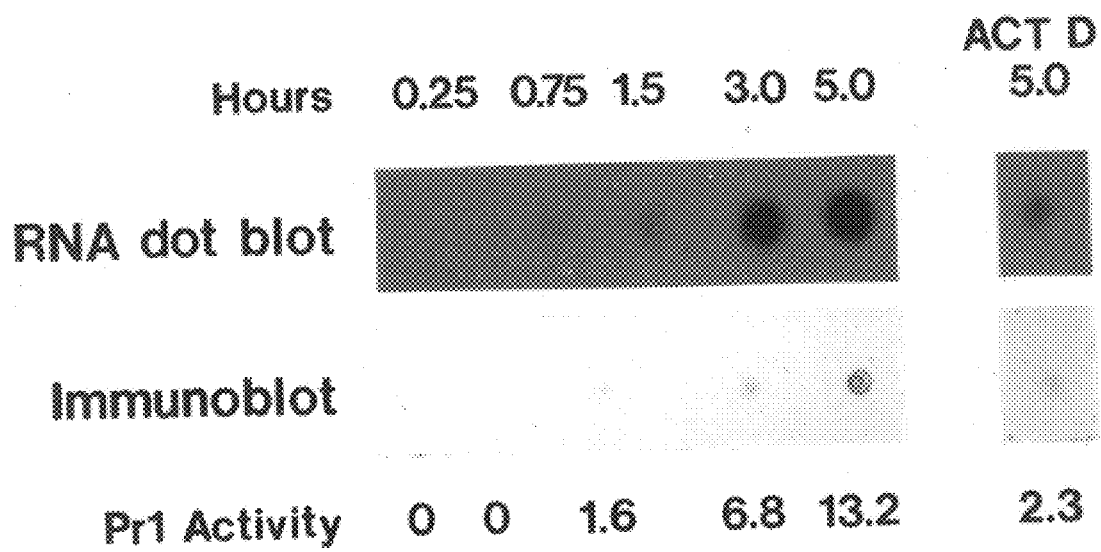

FIG. 3 shows detection of starvation specific RNA species and Pr1 using dot blots. Total RNA was extracted from Metarhizium mycelia transferred from NAG/basal salts media to minimal media for the number of hours indicated above. The RNA wa denatured with glyoxal and dotted to nitrocellulose paper (0.3 $\mu$g in 2 $\mu$l aliquots). The dot blots were hybridized with a [$^{32}$P] cDNA probe for starvation specific mRNA species as reported in the text. A 48 hour autoradiograph is shown. Proteins in filtrates from minimal media cultures were placed in $\mu$l aliquots onto nitrocellulose and probed wi anti-Pr1 serum. The figures underneath the immunoblot represent the corresponding increase in Pr1 activity expressed as nmoles pNP ml$^{-1}$ min$^{-1}$. (Act D), the effects of Actinomycin D (100 $\mu$g ml$^{-1}$) on RNA and Pr1 synthesis.

Within 1 hour after the transfer of mycelium from NAG, starvation specific mRNA transcripts were detectable and the level increased sharply over the next 4 hour (FIG. 3).

Treatment of samples with RNase entirely eliminated binding of the probe further indicating that de novo RNA synthesis was involved. Immunoblot analysis confirmed that the corresponding increase in Pr1 activity represented a true increase in the amount of Pr1 protein in the medium (FIG. 3). Actinomycin D was used at a concentration (100, µg ml⁻) which massively reduces detectable RNA synthesis in Metarhizium ("Production in vitro of appressoria by the entomopathogenic fungus *Metarhizium anisopliae*", by R. J. St. Leger et al, *Experimental Mycology* 13: 274–288, 1989b, incorporated herein by reference.). Addition of Actinomycin D at the beginning of starvation inhibits the de novo formation of unique mRNA and formation of Pr1 (FIG. 3). These results suggest some regulation of gene expression exerted at transcription during starvation. We wondered, however, whether these RNA's could be packaged into spores, perhaps stored for future use.

Figure 4:
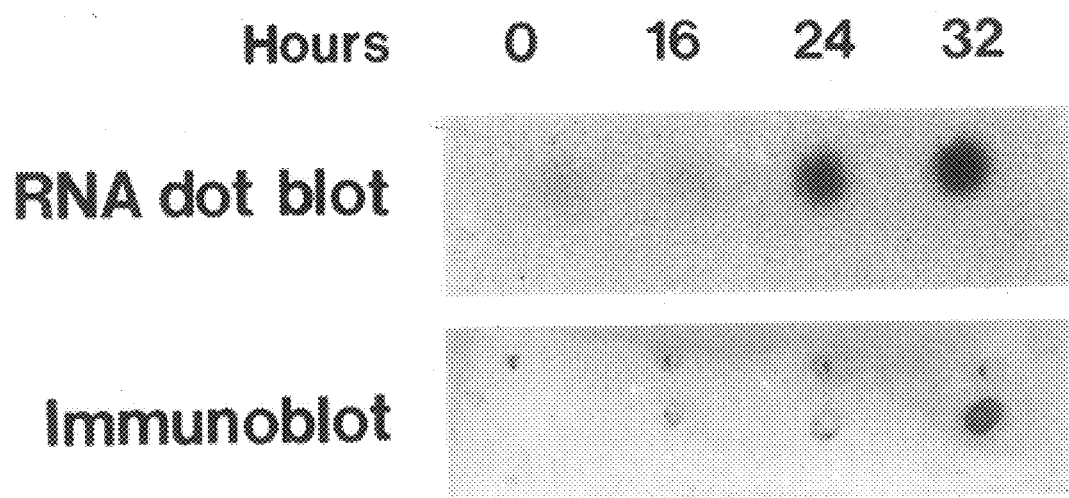

FIG. 4 show detection of starvation specific RNA species and Pr1 during differentiation of appressoria. Total RNA was extracted from germlings differentiating for the number of hours indicated above (O=ungerminated conidia) denatured and dotted to nitrocellulose paper (0.2 µg in 4 µl aliquots). The dot blots were hybridized with a [$^{32}$P] cDNA probe for starvation specific mRNA species. A 72 hour autoradiograph is shown. Proteins extracted from conidia or germlings in lysis buffer were placed in 1 µl pl aliquots on nitrocellulose filters and probed with anti-Pr1 serum.

As shown in FIG. 4, total RNA from fractured spores contained only low levels of mRNA species recognized by the subtraction [$^{32}$P] cDNA probe. By contrast, high levels of messenger were present in germlings-forming appressoria, which correlated with Pr1 production.

Precursors and Processing of Pr1

$^{35}$S incorporation into proteins. [$^{35}$S] methionine incorporation into proteins was studied in mycelia transferred to nutrient deprived media. Mycelia from 3 day old N-acetyl-glucosamine cultures (see below) were collected on Whatman #1 filter paper and washed extensively with distilled water. Mycelia (1 g wet wt) were then resuspended in 10 ml of chitin media (0.5% chitin, 0.1% $KH_2$, $PO_4$, 0.05% $MGSO_4$, pH 5.8) and shaken at 75 rpm at 27.5° C. After 15 min cultures were monitored at 10 min intervals for Pr1 release. For pulse labelling experiments, 0.5 mCi [$^{35}$S] methionine (Trans $^{35}$S, an $^{35}$S labelled bacterial hydrosylate from ICN radiochemicals) was added to cultures and unless otherwise specified the mycelia were further incubated for 5 to 20 min. In some experiments TLCK or Tunicamycin were added at the concentrations given in the text 20 min before the radioactive amino acid was added. For pulse chase experiments, essentially the same procedure was used, except that labelled mycelium was chased with unlabelled methionine (20 mM) plus cysteine (20 mM) at a 4,000-fold excess for the times given in the text.

Labelled mycelia were collected on millipore filters, washed with cold distilled water, and comminuted under liquid nitrogen. The ground mycelium was shaken for 20 min with 5 volumes of lysis buffer (1.1% Triton X-100, 100 mM Tris-HCI (pH 7.8), 10 mM EDTA, 1 mM PMSF, 0.1 mM aprotonin, 0.02 mM TLCK and 0.02 mM leupeptin) at 4° C. Following clarification (8,000 g, 10 min) supernatants were analyzed by immunoprecipitation and by SDS-PAGE as described below. Proteins secreted into growth media were precipitated by incubating overnight at −20° C. with 3 vols. 0.1 M ammonium acetate in methanol containing 1 mM PMSF. Proteins were collected by centrifugation (10, 000 g, 10 min) and redissolved in water.

Figure 5:
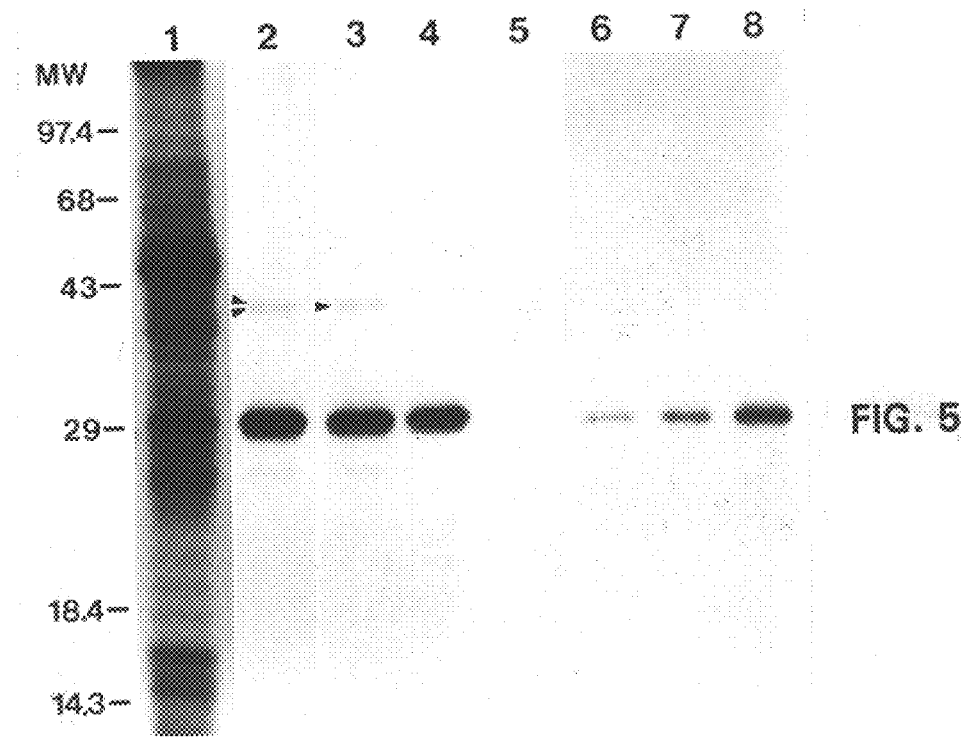

FIG. 5 shows pulse chase analysis on the accumulation of Pr1 and Pr1 precursors by Metarhizium in 3 hour minimal media culture. Mycelia were pulse-labelled with [$^{35}$S] methionine (50,µCi ml⁻¹) for 10 min. Lane 2 shows total labeled proteins extracted from mycelia. Lanes 2–4, the radioactivity was chased with unlabelled methionine for 0 min (control) (lane 2), 5 min (lane 3), or 10 min (lane 4) and the cells were processed and immunoprecipitated with anti-Pr1-serum. The arrow heads indicate two bands (41 and 40.8 kDa) in lane 2 and one band in lane 3. Lanes 5–8, time course of secretion of Pr1 following pulse-labelling with [$^{35}$S]-methionine for 5 min (lane 5), 10 min (lane 6), 15 min (lane 7) or 20 min (lane 8) the culture supernatant medium was precipitated with ammonium acetate in methanol and re-dissolved precipitates immunoprecipitated with anti-Pr1-serum.

Pulse labelling mycelia for 10 min, 3 hour post-transfer to minimal media, allowed resolution of more than 30 proteins, and immunoprecipitation of detectable levels of 41 and 40.8 kDa proteins as well as mature extracellular Pr1 (FIG. 5). Pr1 added to the mycelial lysate before addition of the antibody effectively competed with each of these proteins. We assume, therefore, from the identity of M.wt.'s that the 41 kDa protein represents the primary translation product previously identified by in vitro translation. In two out of four replicates, labelling of mycelia for longer than 5 min revealed a faint low molecular weight band (26.5 kDa) that may or may not be related to Pr1.

The 41 and 40.8 kD precursors were present in very low amounts as compared with the mature protease. This suggested that the precursors are rapidly processed so that the fraction of labelled Pr1 represented by the precursor remains low. Consistent with this, labelling of mycelia for longer than 10 min revealed only the 41 kDa precursor suggesting that the fraction of total label in the 40.8 kDa precursor was almost zero. This hypothesis was confirmed by a pulse chase experiment. After a 10 min chase with cold methionine plus cysteine the fraction of labelled Pr1 represented by the precursors was greatly reduced while levels of mature extracellular Pr1 were almost unaffected (FIG. 5). Neither precursor was detectable in growth media.

The time taken for mycelia to process an amino acid nutrient into mature extracellular Pr1 was determined by precipitating Pr1 secreted into the supernatant medium at various times after the addition of $^{35}$S-methionine to 3 hour minimal media cultures. Labelled extracellular Pr 1 appeared first 5–10 min after addition of the labelled amino acid and increased sharply for the 20 min duration of the experiment (FIG. 5). The Pr1 bands were cut out and their radioactivities were counted in a Scintillation counter. The transit time from addition of label to the appearance of extracellular Pr1 was 6.5–7.2 min calculated from three similar pulse chase experiments by plotting the counts incorporated into the Pr1 bands versus time and extrapolating to zero counts.

Production of active Pr1 was reduced by 63% after a pre-incubation (3 h) with tunicamycin (100 µg m⁻¹) indicating that glycosylation reactions are involved in processing of Pr1; the relative molecular mass of the mature protease was unaffected by tunicamycin, showing a low level of Pr1 glycosylation.

The results described above suggest that a precursor of high M.w. is processed down to the low M.W. active enzyme, presumably by selective proteolytic cleavage. To test for the involvement of the trypsin-like Metarhizium enzyme, Pr2 (St. Leger et al., 1987b) we pre-incubated mycelia (1 h) with the specific Pr2 inhibitor, TLCK. This inhibitor blocks formation of appressoria indicating that it can enter mycelium (unpublished data). Nevertheless, the inhibitor had no effect on production and apparent molecular weight of the Pr1 protein.

Discussion of the Isolation of Translatable mRNA Coding for Pr1

The appearance of Pr1 is accompanied by a similar change in the prevalence of translatable Pr1 transcripts, thus the formation of translatable mRNA is required for the increased rate of Pr1 synthesis. This information, coupled with the lack of transcripts in ungerminated conidia, and our information that inhibition of RNA synthesis inhibits the synthesis of starvation induced transcripts, strongly suggests that the regulation of synthesis of starvation induced proteins is at the level of transcription. Nevertheless since the primary translation product of Pr1 is 11 kDa larger than the mature protease, substantial post-translational processing must be involved in production of active enzyme.

Detection of a 40.8 kDa precursor suggests this may involve multiple steps. High molecular weight proenzymes are the norm among the extracellular proteases of bacteria (Kessler, E. and Satrin, M. (1988). Synthesis, processing and transport of *Pseudomonas aeruinosa* elastase. *Journal of Bacteriology*. 170, 5241–5247, incorporated herein by reference.). They may also be common to proteases of fungi as attested to by the recent demonstration of a very large precursor (76 kDa) for a vacuolar protease (31 kDa) in *Saccharomyces cerevisiae* (Moehle, C. M. et al (1989) Processing pathway for Protease B of *Saccharomyces cerevisiae*. *Journal of Cellular Biology* 108: 309–324.). This contrasts sharply with the primary translation products of fungal cutinase and pectinase which are just 2–3 kD larger than the mature extracellular enzyme (Flurkey, W. H. and Kolattukundy, P. E. (1981). In vitro translation of cutinase mRNA: evidence for a precursor form of an extracellular fungal enzyme. Archives of Biochemistry and Biophysics. 212, 154–161; DeLorenzo, G. et al, (1987) Induction of extracellular polygalacturonase and its mRNA in the phytopathogenic fungus *Fusarium moniliforme*. *Journal of general Microbiology* 133: 3365–3373; both incorporated herein by reference). The function(s) of the large precursor polypeptides are not known, but presumably they keep the cell associated enzyme inactive preventing proteolysis of cell constituents. Consistent with this, Pr1 is very active against components of Metarhizium mycelium after partial disruption of the cell by heating at 85° C. (unpublished data).

Production of Pr1 was allowed by carbon and nitrogen de-repression alone. Rapid growth in nutrient rich media (e.g. SDB) delayed subsequent Pr1 production, as compared with a poorer growth medium, after transfer to nutrient deprivation suggesting that depletion of accumulated nutrient reserves linked to reduced growth rate may be the non-specific signal for Pr1 production. The most rapid initiation of Pr1 synthesis, which occurred within 45–60 min of transfer from NAG medium, is comparable temporally with induction of Metarhizium chitinase by chitin degradation products (30–60 min) (St.Leger, R. J. et al 1986b. Cuticle-degrading enzymes of entomopathogenic fungi: regulation of production of chitinolytic enzymes. *Journal of General Microbiology* 132: 1509–1517, incorporated herein by reference.) and of Fusarium cutinase by cutin monomer inducers (30–45 min) (Woloshuk, C. P. and Kolattukudy, P. E. (1986) Mechanism by which contact with plant cuticle triggers cutinase gene expression in the spores of *Fusarium solani f.sp. pisi*. *Proceedings of the National Academy of Sciences* 83: 1704–1708.). While cutinase transcripts, however, are detectable within 15 min after addition of the inducers, Pr1 transcripts were not observed until 45 min post-transfer. Pr1 production apparently catches up with cutinase production in the short transit time of 6.5–7.2 min. from uptake of labelled amino-acid to extracellular release of mature enzyme. Such rapid secretion implies that in spite of the binding of Pr1 to cell wall components (Goettel et al., 1989) a large component of the enzyme secreted through the cell membrane is not retained by the cell wall for a significant length of time. It therefore appears that the "tighter" form of control for cutinase, involving induction by substrate components (Woloshuck and Kolattukudy, 1986), imparts no significant advantage in terms of rapidity of regulation compared with the "looser", less precise form of control of Pr1 production by CR alone. The difference in mode of regulation must relate to the roles of the two enzymes. Cutinase possesses a narrow specificity and will only be required for a brief period during penetrations of the host plant cell wall and it is therefore energetically conservative for enzyme production to be subject to a high degree of regulatory control being mediated by the cutin component of the wall. By contrast, the broad spectrum proteolytic activity of Pr1 (St. Leger et al., 1987b) may have biological functions before and after host cuticle is breached. Its activity will allow utilization of many insoluble substrates during nutrient deprivation, whether the fungus is living as a saprophyte or pathogen.

Pr1 transcript was the major species novel to starvation-induced cultures, indicating the comparative importance of Pr1 in providing nutrients during starvation conditions as compared with other depolymerases. Other workers have used the two-dimensional electrophoretic technique of O'Farrell, P. H. (1975) High-resolution two-dimensional electrophoresis of proteins, *Journal of biological Chemistry* 250: 4007–4021, incorporated herein by reference, to obtain greater sensitivity of identification of novel proteins. However the very basic nature of Pr1 (pI ca. 10.5; it migrates into the region of the cathode) and the sometimes confusing and contradictory results obtained trying to identify novel proteins (Lovett, J. S. (1987) The molecular biology of fungal development, In *Plant-Microbe Interactions, Molecular and Genetic Perspectives*, Vol. 2. pp. 64–99 (Kosuge, T. & Nester, E. W., eds.) Maci-nillan Publishing Co., N.Y., incorporated herein by reference) led us to use the alternative technique of select-hybridization to identify novel polypeptides. We assume the three transcripts detected represent completely novel mRNA species; even large changes in the abundance of other transcripts should not have been detected because of the exhaustive subtraction hybridization that was performed. The identity of the two Pr1-unrelated-polypeptides has not been identified but Metarhizium produces a wide range of extracellular hydrolases in nutritionally poor media (St. Leger et al., 1986a).

Our results suggest that three translatable transcripts including transcripts for Pr1 are produced within 60 min of nutrient deprivation. Transcripts for Pr1 are the predominant starvation-induced species and translate as a short lived precursor, which is rapidly (<15 min) processed into the much smaller extracellular mature enzyme. We discuss our results in terms of different regulatory strategies, as we were particularly interested in whether Pr1, being under a comparatively looser form of control by catabolite repression (CR) alone, could be regulated as rapidly as those more tightly regulated enzymes induced specifically by the presence of their substrates.

In summary, there appears to be regulation of Pr1 gene expression exerted at transcription during starvation, with production of a high Molecular weight precursor which is rapidly processed to active extracellular enzyme. A translatable mRNA sequence coding for a chymoelastase has been purified and isolated for the first time.

A Pr1 transcript was isolated from fungus capable of producing a Pr1, by: a) growing the fungus on nutrient rich media; b) transferring the fungus to nutrient poor media; c) after 3 hours of growth on the nutrient poor media, extracting mRNA from the fungus; and d) isolating the Pr1 transcript from the extracted mRNA. Proteases of several other important entomopathogens are also produced during nutrient deprivation, suggesting our results may have widespread implications in the understanding of fungal pathogenesis of insects.

Cloning of the Pr1 Gene

To identify genes expressed early in nutrient deprivation, a cDNA library was constructed from mycelia deprived of nutrients for three hours. The library was differentially screened by using cDNA probes from rapidly growing mycelia and nutrient deprived mycelia. A total of 15,000 plaques were screened and 45 clones differentially expressed during nutrient deprivation were identified. Cross-hybridization of these clones resulted in identification of four non-overlapping clone families. Two of these families comprised 26 (class 1) and 15 (class 2) of the clones respectively.

Extraction procedures for RNA. Total RNA was extracted from small fungal samples (conidia and germlings) using guanidine HCI as described previously. Infection structures (appressoria) were induced by germinating conidia in yeast extract media (YEM) (0.0125%) in glass petri dishes as described previously (St. Leger, 1989a). For some experiments, YEM concentration was increased to 0.03% which encourages polar hyphal growth at the expense of appressorium production (St. Leger et at 1988b).

Construction and screening of a cDNA library. The method of obtaining a cDNA sequence which codes for a chymoelastase can be used for a variety of fungi capable of producing chymoelastase. The method comprises: a) inducing a culture to express Pr1; b) isolating mRNA from the culture; c) preparing a cDNA library from the isolated mRNA; and d) differentially screening the cDNA library for genes coding for the chymoelastase.

When rapidly growing mycelium of *M. anisopliae* (isolate ME 1) is transferred to a nutrient poor media, it responds within 3 hours by producing Pr1. Poly (A$^+$) RNA was isolated from cultures 3 hours after transfer from Sabouraud dextrose broth (SDB) to 0.1% chitin media as previously described.

Recombinant plasmids adapted for transformation of a microbial host, wherein the plasmid comprises a plasmid vector into which a DNA sequence which codes for a chymoelastase has been inserted, have been constructed. Complementary DNA was synthesized, EcoR1 methylated and, after addition of EcoR1 linkers, cloned into the EcoR1 site of λgt10 (Invitrogen Librarian Kit).

The λgt10 bank was differentially screened by using labelled cDNA essentially according to standard procedures (Sambrook et al, 1989). This was done at low density (1,000 plaques per petri dish) using duplicate pairs of filters, two hybridized with control cDNA made from SDB cultures and two with cDNA made from cultures transferred for 3 hour to 0.1% chitin media. Positive plaques were selected and purified. Amplified plaques were further screened three times. The inserts of cDNA clones specifically produced in nutrient deprived mycelia were subcloned into the blue script vector (Strategene) for initial analysis (hybridization to a panel of all recombinant clones of interest). A Blue Script Plasmid vector including a DNA sequence insert coding for the amino acid sequence of an enzyme Pr1 was deposited on Jul. 26, 1991, NRRL B-18853.

Figure 6:
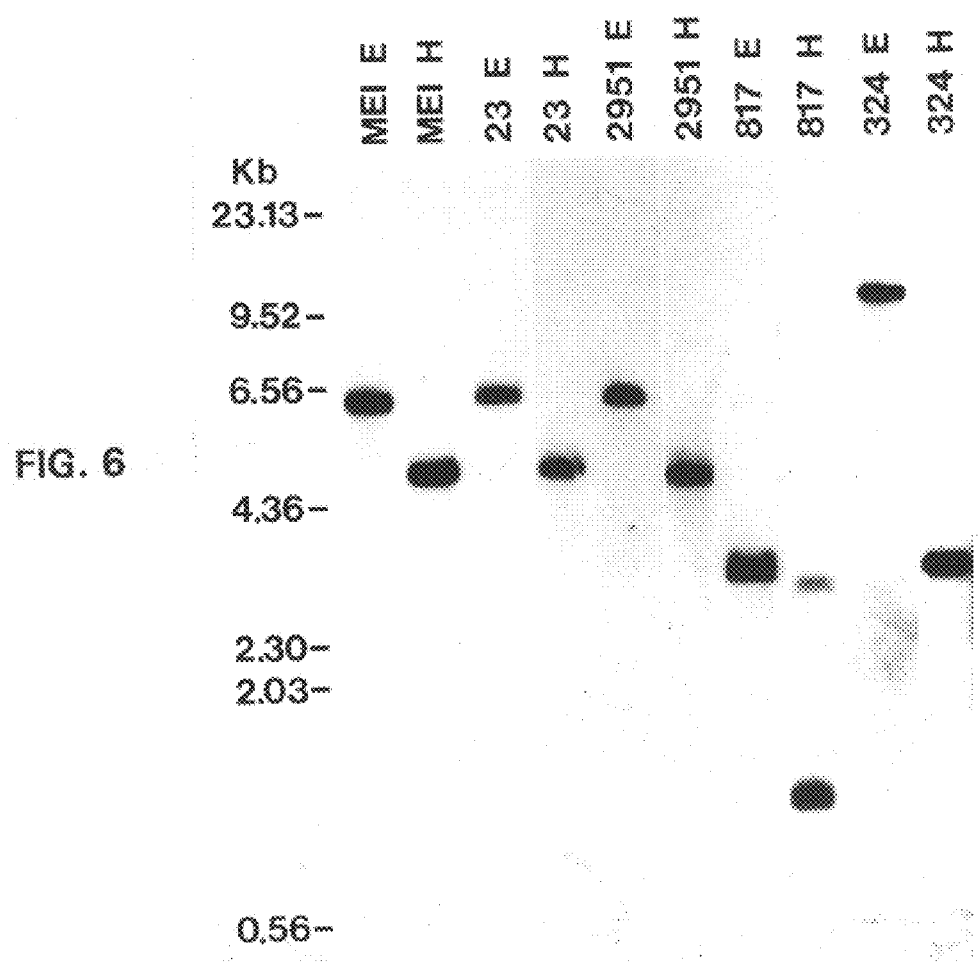

New organisms can be engineered, wherein the organism is the product of an insertion of a gene expression vector including a DNA sequence coding for a Pr1 into a starting organism (e.g. viruses, bacteria, plants, fungi, etc.) such that the new organism is capable of producing said chymoelastase in a recoverable quantity. Currently, primary translation production (Pr1 precursor) is expressed in *Escherichia coli*. A transformed *Escherichia coli* including a Blue Script Plasmid vector including a DNA sequence insert coding for the amino acid sequence of an enzyme Pr1 was deposited, Jul. 26, 1991, NRRL B-18853. *E. coli* does not possess an endogenous secretable protease. By contrast, *Bacillis subtilis* produces subtilisins; proteases related to Pr1. Therefore, *B. subtilus* may be capable of expressing and secreting active Pr1 as distinct from the precursor. It is also possible that as the mechanism for the maturation of chymoelastase is better understood, the precursor could be made active extracellularly.

Southern blot analysis of fungal DNA. Chromosomal DNA from 3 d old SDB cultures of five strains of *M. anisopliae* was isolated by grinding freeze-dried mycelium in liquid $N_2$, stirring gently in extraction buffer (50 mM Tris, pH 8, 10 mM EDTA and 0.5% SDS) extracting with phenol/chloroform (1:1) and chloroform, and precipitating the aqueous phase with isopropanol. Genomic DNA was purified on a CsCl gradient (Sambrook et al, 1989). DNA for each strain was digested with restriction enzymes and fragments separated in 0.8% agarose gels. The DNA was denatured and blotted in 10×SSC onto nylon (Sambrook et at, 1989).

The southern blot analysis showed that four of the longest clones in class I (inserts>1 kb) hybridized to an oligonucleotide probe (5'-GG(X) AT(X) AC(X) $GA^G_A$ $CA^G_A$ where X equals mixed nucleotides to take into account third-base degeneracies in amino acid codons) synthesized from a sequence of amino acid residues (Gly-Ile-Thr-Glu-Gln) at the N-terminus of the purified Pr1 protein.

The longest clone, called λPr1, was sequenced in its entirety. Partial sequencing (350 base pairs from the 5' and 3' end) of the subcloned cDNA inserts in two other clones (called λPr2 and λPr3) indicated that they are different copies of the same mRNA; and, therefore, that Pr1 is not composed of a complex of isozymes. The longest clone in class 2 was designated 'starvation-specific gene', ssg.

Hybridization with oligonucleotide probes and DNA restriction fragments. Oligonucleotides were end-labelled with [$^{32}$P] ATP and T, polynucleotide kinase and used directly for hybridization as described (Sambrook et al, 1989). DNA probes were prepared by oligolabelling of DNA segments using [$^{32}$P]CTP (3,000 Ci/m/mol). In many cases, this was done directly with gel-excised DNA bands as described by Feinberg and Vogelstein (1984) in "A technique for radio labelling DNA restriction endonuclease fragments to high specific activity" *Anal. Biochem.* 137, 266–267. Hybridization was carried out at 42° C. in 50% formai-nide—6× SSPE, 5× Denhardts, 1% SDS, and 100 $\mu$g $ml^{-1}$ salmon sperm DNA. Washes ranged from 2× to 0.1× SSC.

The simple genomic organization of the Pr1 gene is shown in FIG. 6. FIG. 6 shows a southern blot analysis of restricted chromosomal DNA from *M. anisopliae*. DNA isolated from mycelia of five isolates (MEI, 23, 2951, 817 and 324) was digested to completion with EcoR1 (E) or Hind III (H) and separated by electrophoresis on a 0.8% agarose gel. After transfer to gene screen, the DNAs were probed with a Pr1 [$^{32}$P] cDNA plasmid insert, washed in 0.1×SSC, 0.1% SDS, at 68° C., and subjected to autoradiography (4 hours).

After digestion of genomic DNA with appropriate restriction enzymes, only a single fragment hybridized to the λPr1 indicating that the gene is present once in the genome. The same sized fragments were present when DNA from the three American isolates (ME1, 23, and 2951) was digested with EcoR1, Hind III (FIG. 6), Sal1 and EcoRV (data not shown). Different sized fragments were obtained from a European isolate (817) and an Australian isolate (324) (FIG. 6). The Pr1 gene(s) of isolate 817 was digested into small fragments by Hind III indicating that it contains a restriction site for this enzyme.

Sequence of the Pr1 Gene

FIG. 7 shows the nucleotide sequence of the Pr1 cDNA clone λPr1 and its translation into amino acid sequence from an ATG start codon to a termination codon (TAA). ↑, putative signal sequence cleavage site; ↓, prosequence cleavage site. Circles identify the aspartic acid, histidine, and serine residues corresponding to active site residues in the homologous subtilisins. Connected circles identify cysteine residues forming two disulfide bonds in proteinase K ("Amino acid sequence of proteinase K from the mold *Tritirachium album*", by K. D. Jany et al, FEBS. 199, 139–144, 1986). Possible N-linked glycosulation sites and a polyadenylation site are underlined.

Plasmid DNA was isolated with an alkaline lysis procedure and purified on a CsCl gradient (Sambrook et al, 1989). The plasmids were denatured and the cloned cDNA sequenced using the Sequenase Kit (U.S. Biochemical Corp., Cleveland, Ohio). Band compressions in the sequencing gel were resolved by substituting 7-deaza-dGTP in place of DGTP in the reaction mixture.

The first AUG codon of the transcript possesses the essential flanking regions of eukaryotic ribosomal initiation sites (an A at −3 and a purine at +4). The open reading frame (ORF) contained between this AUG and the first termination codon (TAA) is 1164 base pairs long and encodes a 388 amino acid peptide. The calculated MW of 40,366 is in good accordance with the estimate of 41 kDa for the primary translation product of Pr1 as discussed above. The eight amino acid residues from the N-terminus of the mature Pr1 were determined to be Gly-Ile-Thr-Glu-Gln-Ser-Gly-Ala. This sequence was located 107 residues from the N-terminus of the amino acid sequence (FIG. 7). The calculated MW of the mature protease (28,629) is also in close accord with the previously reported estimate of Pr1 of 29 kDa, as discussed above.

Analysis of the N-terminal amino acid sequence of the primary translation product suggested the existence of a signal peptide. The format of the signal includes a charged residue (His), a core of eight hydrophobic residues and a helix breaking residue (Pro), and four residues before a signal peptidase cleavage site (Ala-Pro-Ala). This is consistent with the empirical rules of typical presecretory sequences except that the hydrophobic core is smaller than the nine residues usually regarded as sufficient to span a membrane ("Compilation of published signal sequences" by M. E. E. Watson, *Nucleic Acids Research* 12, 5145–5159, 1984.). The remaining sequence of amino acids between the signal peptide and the mature protease would be the pro-region found in some proteases.

The predicted mature protease contained one potential N-glycosylation site ($Asn_{151}$-Thr-Ser), which follows the general rule of Asn-X-Thr/Ser where X is any residue except perhaps Asp (Hubbard, S. C. and Ivatt, R. J. 1981 "Synthesis and processing of asparagine-linked poly-saccharides" Ann. Rev. Biochem. 50, 555–583, incorporated herein by reference.) and two Ser-Thr base pairs (Ser-22 and Ser-193) which are potential sites for O-glycosylation. The pro-region lacked sites for glycosylation.

A recombinant DNA sequence coding for a chymoelastase can be engineered, wherein the recombinant DNA sequence has been synthetically altered to change a function or structure of the chymoelastase. The activity of Pr1 is dependent on the enzyme binding to substrate and subsequent hydrolysis. An increase of the positive charge on surface segment of Pr1 by susbstituting positively charged residues (Arg, Lys, His) for neutral or acidic residues could improve binding capabilities. Substitutions in the active site of chymoelastase could change substrate specificity of said chymoelastase. For example, a new amino acid could by substituted at the bottom of the cleft in the active site in place of alanine. Larger amino acids (e.g. glycine or tyrosine) would reduce the size of the optimum substrate. Sythetically altered recombinant DNA sequence coding for chymoelastase could also be engineered, wherein a substrate activity rate of the chymoelastase was modified.

Figure 9:
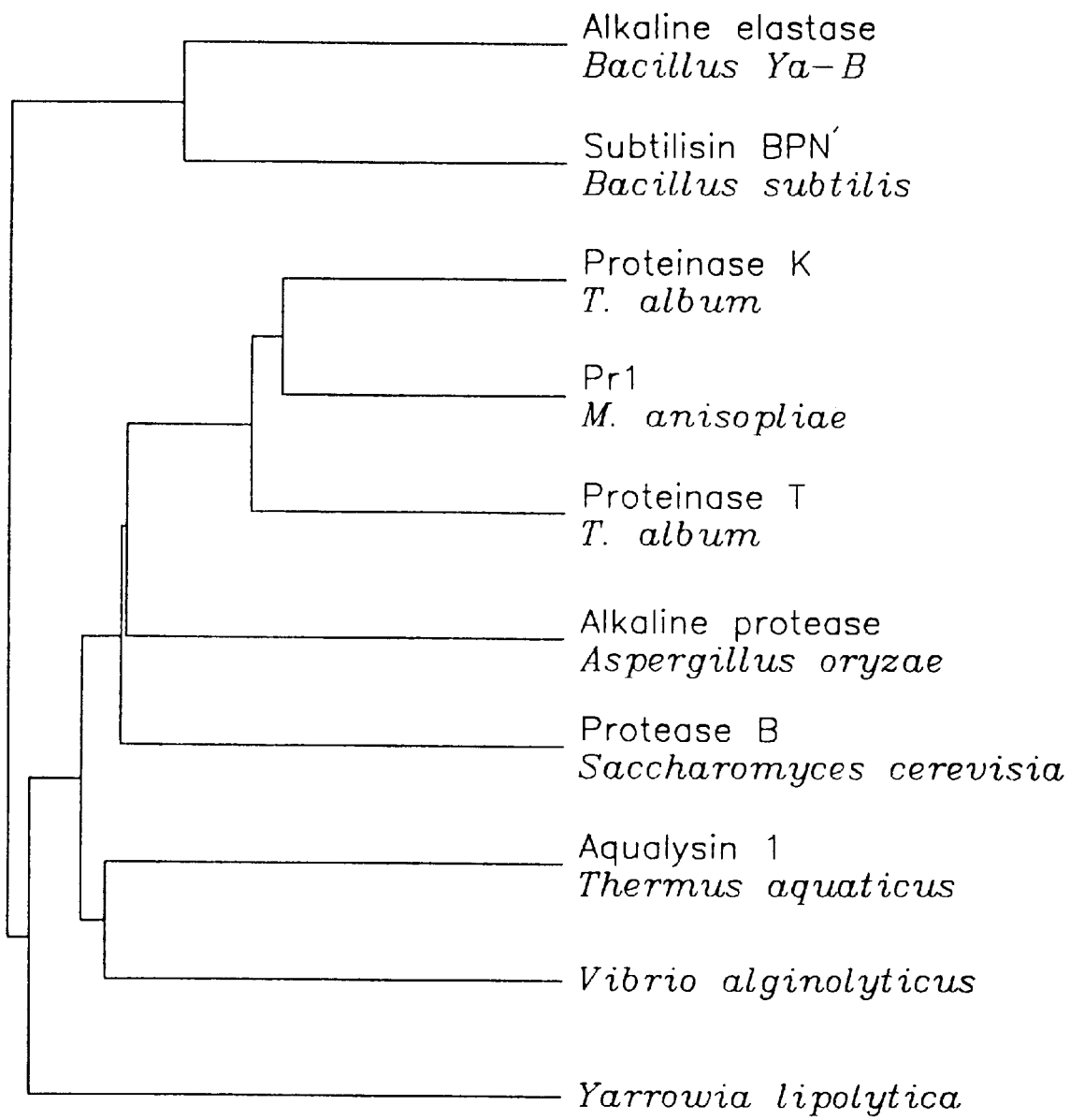

Fragments and derivatives of a DNA sequence coding for chymoelastase, could be used in coding for subunits of a chymoelastase or other polypeptides having an activity which can: a) bind to insect cuticle; b) enhance signal processing of proteins; c) hydrolyse polypeptides; d) suppress protease expression; or e) be used as a probe to identify homologous genes in organisms.

Codon usage. The codon usage in the Pr1 gene shows a very marked bias, as is true in nearly all highly expressed genes from filamentous fungi (Gurr, S. J., Unkles, S. E. and Kinghorn, J. R. 1988 "The structure and organization of nuclear genes in filamentous fungi" In: Gene Structure in Eukaryotic Microbes (Kinghorn, J. R., ed.) IRL Press, Oxford pp. 93–139, incoporated herein by reference). As a rule, whenever possible, a T or a C is preferred at the third positions. Of all codons used in the Pr1 gene, 43% end with a C and 36% end in a T, 16% end with a G and only 4% of the codons used in Pr1 end with an A.

Homology comparison. The predicted protein sequence of the pro-Pr1 shares extensive homology to members of the subtilisin family of serine proteases. FIG. 8 shows homology between pro-Pr1 and the subtilisin family enzymes proteinase K and subtilisin BPN' (Watson, 1984). Identical amino acids are linked. Dashed lines indicate amino acids shared by Pr1 and subtilisin but not proteinase K. Arrows indicate clearage sites for the signal and pro-sequences of Pr1 and proteinase K. The secondary structure predictions for Pr1 and proteinase K, according to the algorithm of Chou-Fasman ("Prediction of protein confirmation", by Chou, P. and Fasman, G. *Adv. Enzymol*, 47, 145–147, 1978) are also shown. Lines indicate -helices, dots indicate -sheets.

The pro-Pr1 shows 61.1%, 44.4%, 43.2%, and 30.2% homology to Tiltirachium album proteinase K (Gunkel and Garren, 1989), yeast (*Saccharomyces cerevisiae*) protease B precursor (Moehle, C. M. et al, 1987 "Protease B of the lysosome-like vacuole of the yeast *Saccharomyces cerevisiae* is homologous to the subtilisin family of serine proteases" *Mol. Cell. Biol*. 7, 4390–4399, incorporated herein by reference.), *Aspergillus oryzae* alkaline proteinase precursor ("A full length cDNA clone for the alkaline protease from *Aspergillus oryzae*: Structural analysis and expression in *Saccharomyces cerevisiae*", by H. Tatsumi, H. et al, *Mol. Gen. Genet*. 219, 33–38, 1989, incorporated herein by reference.), and *Bacillus amyloliguefaciens*, Subtilisin BPN' Precursor (Wells, J. et al, "Cloning, sequencing and secretion of *Bacillus amyloliquefaciens* subtilisin in *Bacillus subtilis*" *Nucleic Acids Research* 11, 7911–7925, 1983, incorporated herein by reference.).

The degree of homology often corresponds to the genetic distance between the enzymes sources. FIG. 9 shows a pile up of nine microbial proteases. Pr1 is compared with alkaline elastase ("Molecular cloning of the structural gene for alkaline elastase YaB, a new subtilisin produced by an alkalophilic Bacillus strain", by R. Kaneko et al, L Bacteriol. 171, 5232–5236, 1989.), subtilisin BPN', proteinase K ("Proteinase K from Tritirachium album Limber", by Gunkel, F. A. and Garren, H. G, Env. J. Biochem, 179, 185–194, 1989.), alkaline protease, protease B ("Cloning and expression of the gene encoding a novel proteinase for Tritirachium album Limber", by B. B. Samal et al, Gene 85, 329–333, 1989.), aqualysin 1 (Tatsumi, 1989), and proteases from V. alginolyticus ("Nucleotide sequence of the Vibrio alginolyticus calcium-dependent, detergent-resistant alkaline serine exoprotease A", by S. M. Deane et al, Gene 76, 281–288, 1989.) and Y. lipolytica ("Cloning and sequencing of the alkaline extracellular protease gene of Yarrowia lipolytria", by L. S. Davidow et al, J. Bacteriol. 169, 4621–4629, 1987.).

The most extensive homologies are between the enzymes from M. anisopliae and T album, both members of the Moniales (deuteromycetes). Progressively less homology is shown with enzymes from Ascomycetes (A. oryzae and S. cerevisae), gram-negative bacteria (Vibrio alginolyticus and Thermus aquaticus) and gram-positive bacteria (Bacillus spp.). Conversely, the protease from the yeast Yarrowia lipolytica showed less overall homology to Pr1 than those from gram-negative bacteria.

The pro-Pr1 shows least sequence homologies with other subtilisin-like enzymes in the pro-region. Two sequences of the pro-enzyme of proteinase K are conserved with subtilisins (Tyr-Ile-Val-Gly-Phe-Lys and Ala-Thr-Leu-Asp-Glu) but only the former is conserved in Pr1[Tyr(−66)-Lys-(−61)] indicating that the sequence Ala-Thr-Leu-Asp-Glu may not play a crucial role in maturation of protease proteins as previously suggested (Gunkel and Garren, 1989). The highest homologies were found in regions previously identified in subtilisins as the serine, histidine and aspartyl components of the active site which comprise the charge relay system crucial for activity in serine proteases (Kraut, J. 1977 "Serine proteases: Structure and mechanism of catalysis" Ann, Rev. Biochem. 46, 331–358, incorporated herein by reference). Interestingly, the fungal enzymes shared a deletion of three amino acids residues which we present in the corresponding sequence of subtilisin (165–167)(FIG. 8). Gly-166 occupies the bottom of the $S_1$ substrate pocket in subtilisin (Estell, D. et al, 1986, "Probing steric and hydrophobic effects on enzyme-substrate interactions by protein engineering" Science 233, 659–663, incoporated herein by reference). Its deletion results in an alanine residue occupying the bottom of the cleft in Pr1. According to the model of Estell et al. (1986), the replacement of glycine by alanine should reduce effectiveness against tyrosine but increase effectiveness against other residues with phenylalanine being the optimum substrate. This is consistent with our previous results (St. Leger et al., 1987). The two sequences which form the sides of the $S_1$ pocket also occur in regions of strong sequence consensus and are made up of the side chains of Ser 115-Leu 116-Gly 117 and Ala 141-Ala 142-Gly 143 respectively in Pr1. The highly conserved Asn 144 (in Pr1) is important in subtilisins for stabilization of the reaction intermediate formed during proteolysis (Kraut, 1977).

Figure 10:
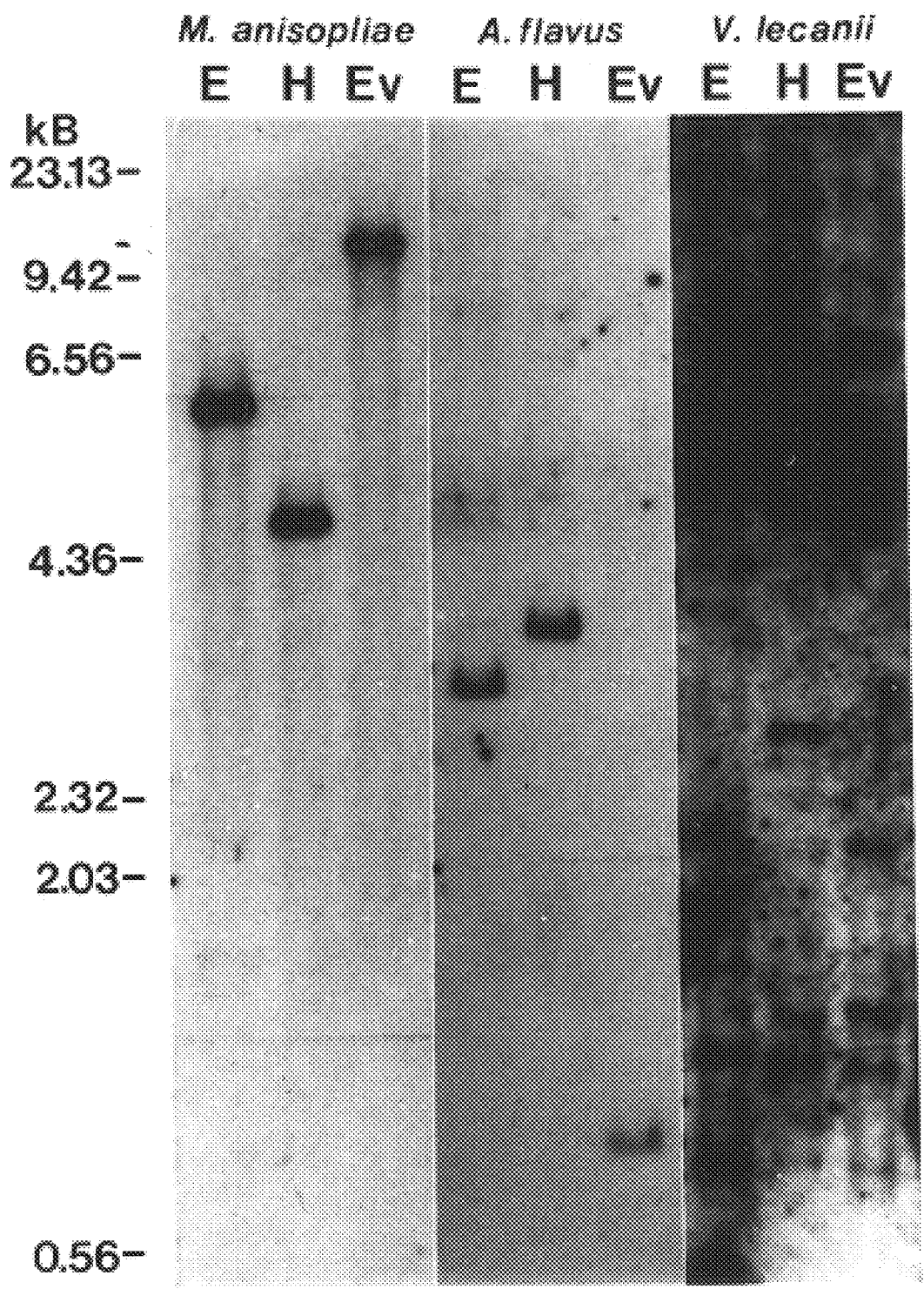

Southern blot analysis was used to identify genes homologous to Pr1 in other entomopathogens. FIG. 10 shows a southern blot analysis of restricted chromosomal DNA from M. anisopliae (MEI), A. flavus and V. lecanii. DNA was digested to completion with EcoR1 (E), Hind III (H) or EcoRV (EV) and separated by electrophoresis on a 0.8% agarose gel. After transfer to gene screen, the DNA's were probed with a Pr1 [$^{32}$P] cDNA plasmid insert, washed in 0.3×SSC, 0.1% SDS, at 47° C., and subjected to autoradiography for 4 hours (M. anisopliae), 20 hours (A. flavus) and 72 hours (V. lecanii).

Compared with digested DNA from M. anisopliae, some weaker cross-hybridizing bands with λPr1 were found in the deuteromycete V. lecanii and the ascomycete A. flavus. No hybridization was detected with DNA from the zygomycete Z radicans at the moderate stringency tested. Hybridaztion to EcoR1, Hind III and EcoRV-cut V. lecanii DNA revealed 5, 6 and 3 major cross-hybridizing DNA fragments, respectively, suggesting the presence of multiple protease genes in the genome. By contrast, A. flavus resemebled in M. anisopliae apparently harboring only one protease gene hybridizing with λPr1. Hind III appears to cut within the protease gene of A.flavus as the major fragment is too small to represent a single gene copy.

Secondary Structure of Pr1

The tertiary structures of subtilisins and proteinase K have been determined (Betzel, C. et al, 1986 "Active site geometry of proteinase K" FEBS, 197, 105–110, incorporated herein by reference). Computer-generated predictions of secondary structure and hydrophilicity of Pr1 are compared with data-derived from the primary sequence of proteinase K (Gunkel and Garren, 1989). The preprotease amino sequence was compared with all other sequences in the Fasta database as described (Pearson, W. R. and Lipman, D. J. 1988, "Improved tools for biological sequence comparison" Proc. Natl. Acad. S@i 85, 2444–2448, incoporated herein by reference). Protein secondary structure predictions were determined using the pep plot program by Gribskov and Devereux (1986) "PEP PLOT, a protein secondary structure analysis program for the UWGCG sequence analysis software package" Nucl. Acids Res. 14, 327–334, incorporated herein by reference, and the peptide structure program by Jameson and Wolf (1988) "The antigenic index: A novel algorithm for predicting antigenic determinants" CABIOS 4, 181–186, incorporated herein by reference.

Figure 11:
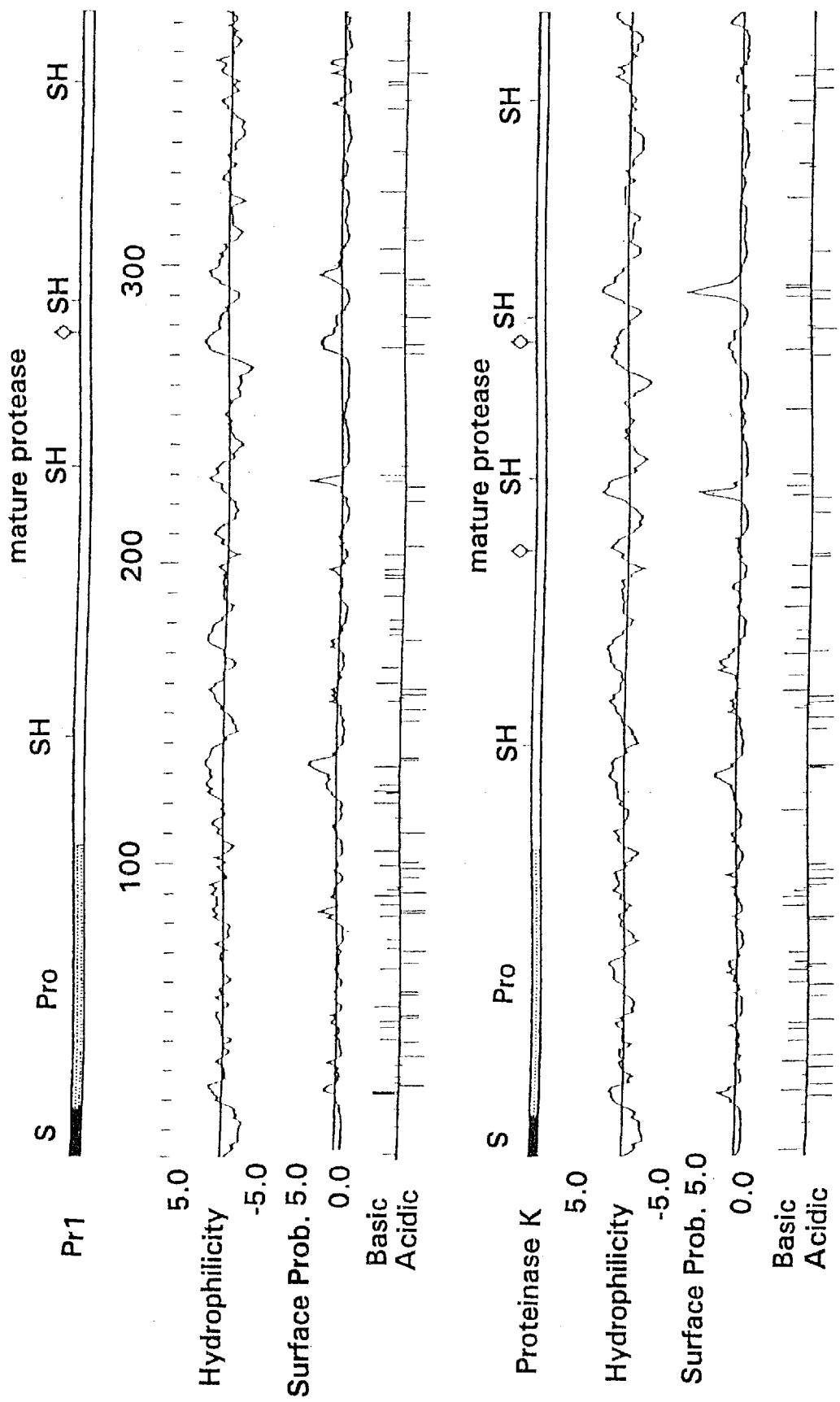

FIG. 11 shows a computer-aided secondary structure analysis of the predicted pro-Pr1 peptide. Hydrophilicity was determined by the method of Kyte and Doolittle ("A simple method for displaying the hydropathic character of a protein", by Kyte, J. and Doolittle, J. Mol. Biol. 157, 105–132, 1982.). Surface probability was calculated according to a formula of Emini et al. ("Induction of hepatitis A virus-neutralizing antibody by a virus-specific synthetic peptide", by E. A. Emini et al, J. Virol- 55, 836–839, 1985.). The α-helix and β-sheet confirmations were predicted by the method of Chou and Fasman. The location of the four cysteine residues and the potential Asn linked glycosylation accepter sequence are indicated.

Proteinase K resembled Pr1 in possession of an initial, highly hydrophobic signal peptide (FIG. 11). However, the signal peptide of Pr1 is distinctive in that, according to the algorithm of Chou and Fasman (included in FIG. 8) and Robson-Garnier predictions (data not presented), it forms an α-helix, rather than the typical β-sheet. In spite of comparatively little homology between primary sequences, both Pr1 and proteinase K show extended regions of α-helix in the pro-region which terminates just before the N-termini of the mature polypeptide (FIG. 11). It is evident from Figure that the hydropathy and surface plot patterns of the mature Pr1 and proteinase K resemble each other indicating similarities in the folding patterns of the two proteins. Only short sequences of secondary structure are predicted within the polypeptide sequences of both mature Pr1 and proteinase K. Proteins possessing this feature frequently contain disulfide bonds, are mainly extracellular, and include structures that can bind polysaccharides (Rossman, M. G. and Argos, P. 1981 "Protein folding" Ann. Rev. Biochem. 50, 499–532 incorporated herein b reference). The α-helix containing the active site Ser 207 (in Pri, FIG. 7), corresponds to the α-helix present in subtilisin BPN which presents this Ser residue to the active site (Wright, C., Alden, R. and Kraut, J. 1969 "Structure of subtilisin BPN' at 2.5 Angstrom resolutions. Nature (London) 221, 235–242, incorporated herein by reference). Some secondary structures were predicted in only one of the two proteases, Pr1 and Proteinase K. Further studies will be required to confirm whether these differences are real or artifactual due to unreliability of the Chou-Fasman prediction methods.

The four cysteine residues comprising the disulfide bonds in proteinase K (Jany et al, 1986) are preserved in Pr1 suggesting that the disulfide bridging patterns are largely similar. Also, they are embedded in the Pr1 molecule (FIG. 11) consistent with the formation of disulfide bonds. Conversely, the Asn-linked glycosylation site is on the surface of the Pr1 molecule making glycosylation possible. Of the twenty-seven positively charged residues and eighteen negatively charged residues in the mature Pr1, fourteen and eight respectively are located on the protein surface. Of particular note are His-17, Arg-18, Lys-20, and Arg-26 (in Pr1) which replace non-charged residues or tyrosine in proteinase K (FIG. 8). Apart from this segment and the prediction that proteinase K possess four more acidic residues on its surface than Pr1, the distribution of charged residues is broadly similar in the two proteases.

Timing of mRNA Induction

Nuclear run-on experiments were performed to determine transcription rates over time of the two major starvation-specific mRNA species, Pr1 and Ssg. Nuclei were isolated from catabolite repressed cells grown in nutrient rich media (SDB) and from cells transferred from SDB to minimal media (MM, 0.1% $KH_2PO_4$, 0.005% $MgSO_4$) for up to 72 h.

Run-on transcription. Nuclei were isolated and assayed by modification of previously described procedures for Neurospora (J. J. Loros and Dimlap, 1991, "Neurospora crassa clock-contorlled genes are regulated at the level of transcription", Mol. Cell. Biol. 11, 558–563; and J. V. Paietta, 1989 "Molecular cloning and regulatory analysis of the aryisulfatase structural gene of Neurospora crassa, Mol. Cell. Biol. 9, 3630–3637; both incorporated herein by reference.). Mycelial samples were disrupted in a bead beater containing extraction buffer (1 M sorbitol, 7% [wt/vol] Ficoll, 20% [vol/vol] glycerol, 5 mM $MgCl_2$, 10 mM $CaCl_2$, 0.2 mM PMSF, 1% Triton x-100), centrifuged at 1,500×g for 10 min and the nuclei in the supernatant were pelleted at 15,000×g for 10 min. Assay mixes contained 10 mM Tris (pH 8), 10 mM $MgCl_2$, 2 mM $MnCl_2$, 200 mM KCl, 0.5 mM dithiothreitol, 10% glycerol, 0.05 mM each ATP, CTP, and GTP, 200 µCi of [$^{32}$P] UTP (3,000 Ci/mMol) and 5×10$^7$ nuclei.

Incubations were for 30 min at 30° C. Incorporation of [$^{32}$P] UMP into trichloracetic acid-precipitable product was determined (Sambrook et at, 1989). The synthesized RNA was extracted and ethanol precipitated and 5×10$^7$ cpm was used for hybridization to 10 µg of alkali denatured DNA bound to nitrocellulose fibers as described (Sambrook et at, 1989). Hybridizations were carried out in 50% formamide 5×SSC–1×Denhardts solution–0.1% SDS. Washes ranged from 2× to 0.1×SSC. α-Amanitin (an inhibitor of RNA polymerase 11) added to the transcription mix (0.5 mg ml$^{-1}$) blocked the synthesis of RNA that hybridized to Pr1 and Ssg. DNA and demonstrated the specificity of the system. (α-Amanitin reduced total RNA synthesis by approximately 45%.

Northern blots. RNAs for northern blots were denatured with glyoxal and dimethylsulfoxide (Sambrook et at, 1989). The gels were blotted to nylon and hybridized as for southern blots.

Figure 12:
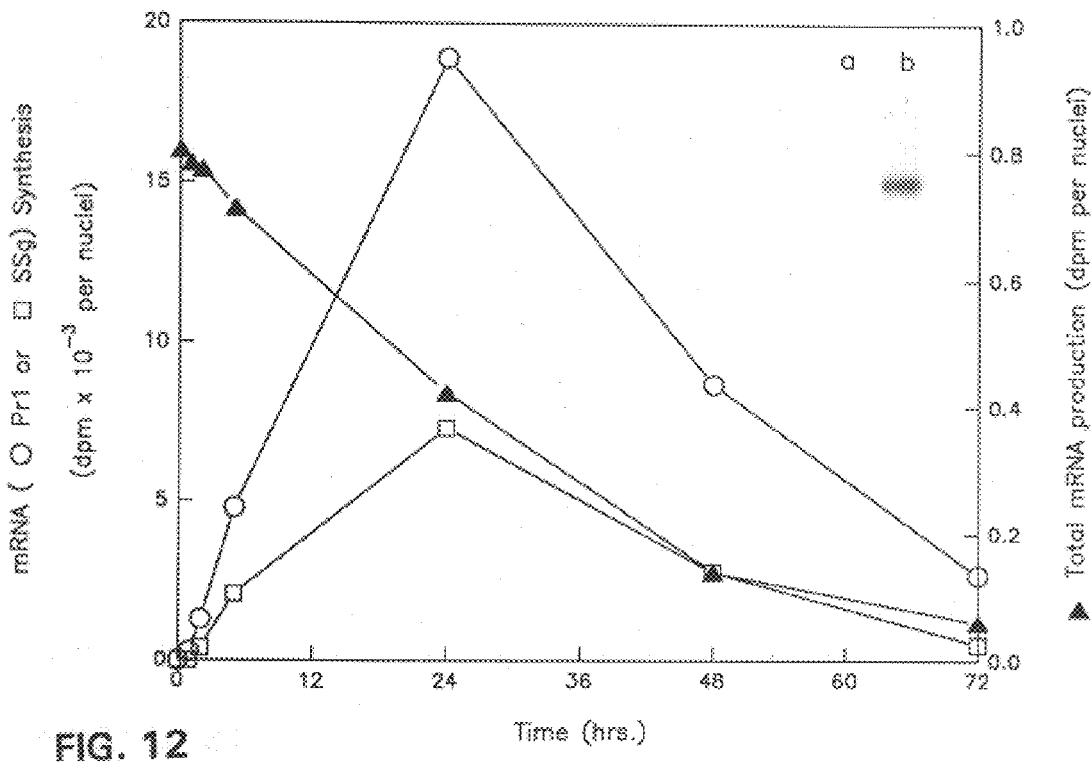

FIG. 12 shows the regulation of synthesis of Pr1 and Ssg. genes at the level of transcription during nutrient deprivation. Nuclear run-on analyses were carried out and the $^{32}$P-labelled RNA was isolated. Transcripts specifically arising from the EcoRI fragments containing the two genes were isolated by hybridization to EcoRI DNA fragments immobilized to filters containing these genes and quantified in a scintillation counter. Total RNA production was determined from [$^{32}$P] UMP incorporation into TCA precibitable product. Counting error (2 standard deviations) was 5% or less. Insert: Sensitivity of the nuclear run-on reaction to the presence of a-amanitin. EcoRI digested λPr1 (1 µg) was agarose gel electrophoresed. The blots were probed with "P-labelled transcripts isolated from nuclear run-on reactions carried out in the presence (A) or absence (B) of 1 mg of α-amanitin per ml.

The transcription rates for Pr1 and Ssg. were compared with total RNA synthesis (FIG. 12). Both Pr1 and Ssg. mRNA are absent in rapidly growing cells in nutrient rich cultures but are produced rapidly (<2 h) when cells are deprived of nutrients reaching a maximum concentration after 24 h. Novobiocin did not effect mRNA synthesis (data not shown), indicating that there is no initiation of RNA synthesis in our isolated nuclear system. Synthesis of both species remains high <48 h even though starvation produces a fall in the absolute level of RNA synthesis.

From repetitions of these experiments, we have concluded that the peak of Pr1 transcription is always greater than that of Ssg. even though the phases of the peaks a very similar for the two genes. As starvation proceeds (48–72 h), there is a sharp fall in transcription of both genes. To analyze the composition of mRNA from starved cells, poly (A$^+$) mRNA was isolated from derepressed cells and translated using a rabbi reticulocyte system.

Figure 13:
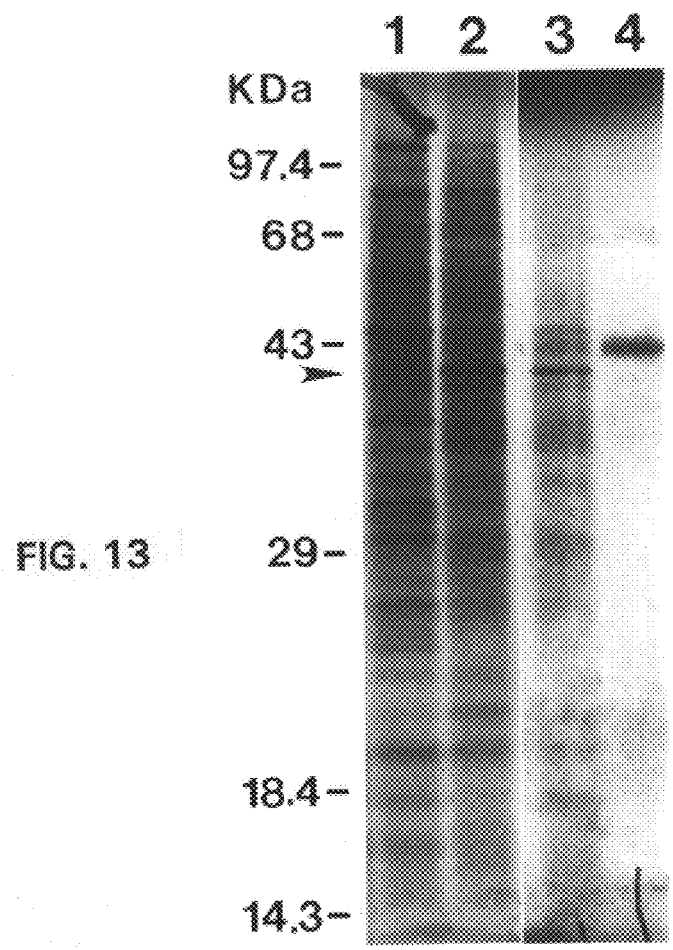

FIG. 13 shows changes in the mRNA population during nutrient deprivation. Protein coding capacities of poly (A$^+$) RNA isolated from Metarhizium transferred from SDB to minimal medium (0.01% $KM_2$ $PO_4$, 0.005% $MgSO_4$) for 20 min (lane 1), 18 hour (lane 2), 48 hour (lane 3) and 72 hour (lane 4). The arrow indicates the position of the primary translation product of Pr1 determined by immunoprecipitation with antiPr1 serum as described previously.

Pr1 (41 kDa) is the predominant induced species up to 48 hour of nutrient deprivation. Post-48 h, the quality of poly (A$^+$) RNA had deteriorated with a novel 43 kDa protein clearly predominating. Immunoprecipitation experiments with anti-Pr1 serum confirmed that the unidentified 43 kDa protein is immunologically unrelated to Pr1.

Pr1 is produced at high levels by Metarhizium germlings induced to differentiate infection structures (appressoria) by nutrient deprivation (St. Leger et al, 1989b). To assay Pr1 and Ssg. transcript levels, total RNA was isolated from conidia, non-differentiating germlings, and differentiating germlings. Northern blots were then prepared and probed with λPr1 and ssg.

Figure 14:
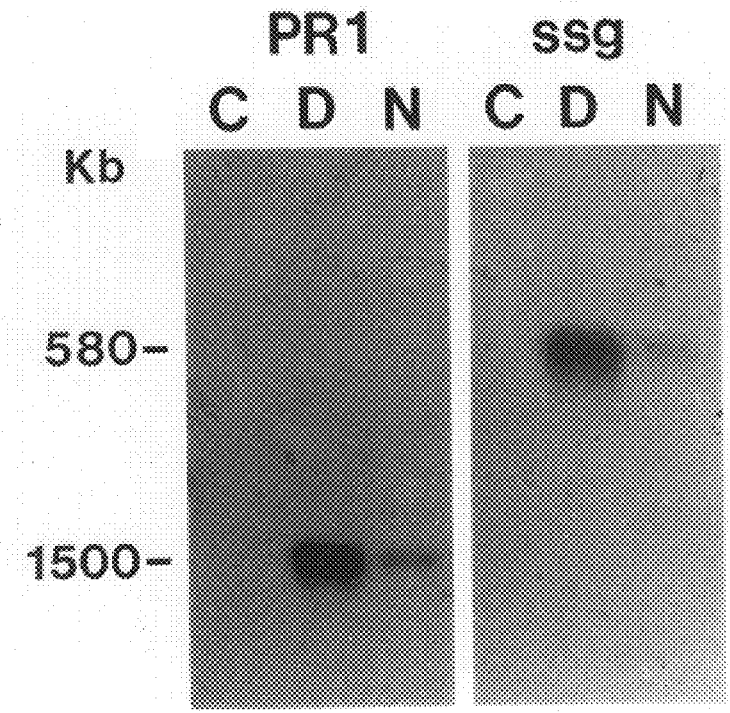

FIG. 14 show the detection of Pr1 and Ssg. mRNA during differentiation of appressoria. Total RNA was extracted from conidia (C) and from germlings grown for 24 hour in 0.0125% YEM (producing appressoria D) or 0.03% YEM (producing non-differentiated hyphal growth N). The RNA (3 mg) was electrophoresed, blotted, and probed with $^{32}$P-labeled EcoR1 fragments from λPr1 or Ssg. plasmids.

Only faint hybridization was detectable in conidia and non-differentiated cells. Compared with non-differentiated cells, an approximately 20-fold and 35-fold increase (by densitometry) in Ssg. mRNA (580 bp) and Pr1 mRNA (1500 bp) were observed, respectively, during differentiation of appressoria. Use of the constitutively expressed fl-tubulin gene as a control probe showed that bulk RNA levels in the non-differentiated and differentiated cells were comparable.

TABLE 2

Relative cuticle degrading and proteolytic activities of Pr1 and proteinase K.

| Substrate | Pr1[a]<br>n = 5 ± SE | Proteinase K[a]<br>n = 5 ± SE |
|---|---|---|
| Suc-(Ala), Pro Phe pNA[b] | 2.3 ± 0.14 (1)[d] | 1.8 ± 0.16 (0.78) |
| Suc-(Ala), Val Ala pNA[b] | 0.21 ± 0.03 (0.62) | 0.34 ± 0.05 (1) |
| M. sexta cuticle[c] | 24 ± 3.4 (1) | 12.5 ± 2.6 (0.52) |
| Salt ext. tf. sexta cuticle[c] | 3.8 ± 0.3 (1) | 0.12 ± 0 (0.03) |
| casein[c] | 59 ± 3.4 (0.97) | 61 ± 4.1 (1) |

[a]Activities were assayed with 5, μg ml − 1 enzyme concentration. Similar results were obtained with enzyme concentrations of 2.5 and 10 μg ml − 1. Controls contained autoclaved enzyme.
[b]Assays against p-nitroanilide (pNA) substrates were performed at 23° C. in 10 mM Tris-HCl (pH 8), 4% (v/v) dimethylsulfoxide, 0.06 mM substrate. Activities are expressed as pmol pNA min − 1 ml − 1.
[c]Activity against protein substrates were determined at 23° C. in 10 mM Tris-HCI (pH 8) containing 2.5 mg ml − 1 protein. Following incubation (30 min), the absorbance of trichloroacetic acid soluble products was read at 280 nm. Enzyme activities are expressed as μg tyrosine equivalents min − 1 ml − 1.
[d]Relative activity (1 = maximum activity).

Substrate Specificity of Proteases

The activities of Pr1 and proteinase K against M. sexta cuticle and other substrates were compared (Table 2). Pr1 was almost 2-fold more effective than proteinase K in degrading intact cuticle. Extraction of loosely (electrostatically) bound proteins produced a more refractory substrate for both enzymes, particularly proteinase K which was 33-fold less effective than Pr1 in degrading extracted cuticle. Both Pr1 and proteinase K rapidly (<30 min) hydrolyzed the complex mix of solubilized cuticle proteins.

Figure 15:
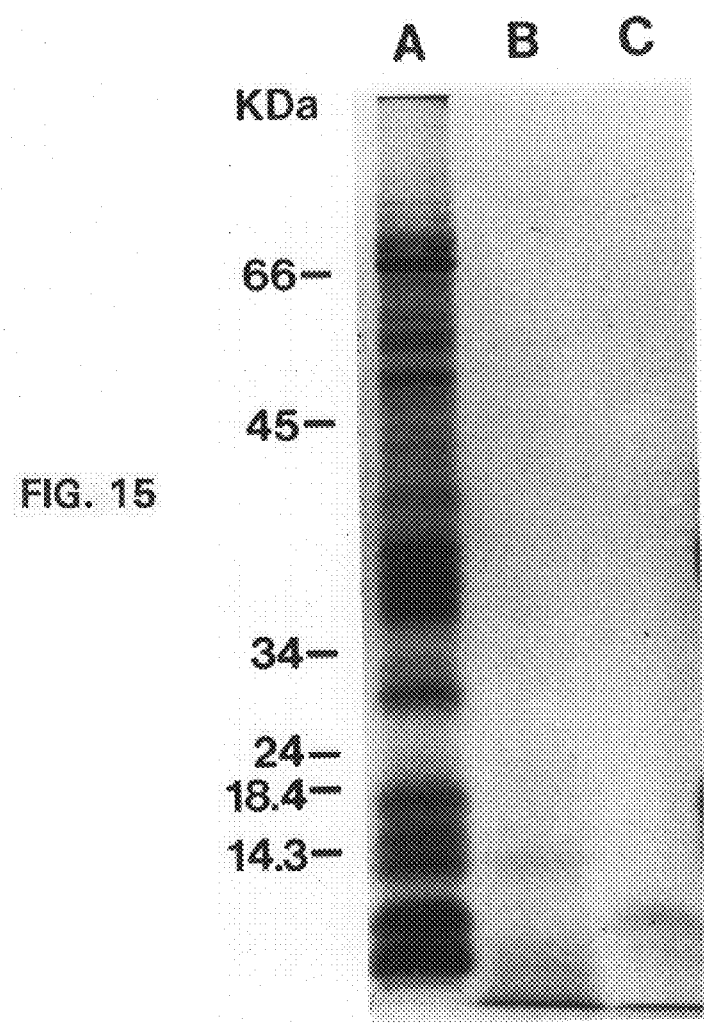

FIG. 15 shows the activities of Pr1 and proteinase K against proteins extracted from cuticles of Manduca sexta. Proteins were extracted from cleaned cuticles of larval M.sexta, dissolved in water, and a sample (40 tig protein) separated by SDS-PAGE (lane 1). Assays were performed at 23° C. in 10 mM Tris-HCI (pH 8) containing 11 mg ml$^{-1}$ extracted protein and 2 μg ml protease. Following incubation (30 min. at 30° C.), the extent of protein digestion by Pr1 (A) and proteinase K (B) was determined by SDSPAGE (40 μg protein per lane). Protein bands were stained using Coomassie blue.

Evidently, the efficacy of Pr1 in assisting cuticle penetration by the pathogen does not depend on specific cuts in select cuticle proteins, but in a broad non-specific activity against multiple proteins. Pr1 and proteinase K are similar in being good general proteases with activity against casein and nitroanilide substrates for elastases (Suc-(Ala)$_2$-Val-Ala-pNA) and chymotrypsins (Suc-(Ala)$_2$-Pro-Phe-pNA).

Preparation of cuticle substrates. Clean samples of cuticle from 3-d-old fifth instar Manduca sexta larvae were prepared as described previously (St. Leger et al, 1988b). Proteins bound by electrostatic or hydrophobic bonds were extracted by washing cuticles of M. sexta in 10 mM Tris-HCl, pH 7.5 containing 0.5 m kCl (Hackman, R. H. 1980 "Biochemical Methods (Proteins) In: Cuticle Techniques in Arthropods (Miller, T. A., ed.) Springer-Verlag, NY pp. 145–184, incorporated herein by reference). Extracted proteins were precipitated by incubating overnight at −20° C. with 3 vols 0.1 M ammonium acetate in methanol. Proteins were collected by centrifugation (10,000 g, 10 min) and redissolved in water. The extracted cuticle was washed by repeated centrifugation (2,000 g, 5 min) with water and dried in vacuo.

Enzyme assay. Nonspecific protease activity (vs. casein), cuticle-degrading activity (vs. M. sexta cuticle), and anilidase activity (vs. blocked peptide nitroanilides) were determined as described in St. Leger et al (1987a). Assays were performed in duplicate. All results are representative of at least two similar experiments using different Miscellaneous. Pr1 was purified to homogeneity as previously described in St. Leger et al (1987a). SDS-PAGE analysis was performed according to St. Leger et al. (1989a). Except where indicated in the text, all chemicals were from Sigma. The proteinase K preparation was Sigma's molecular grade reagent (P4914).

Discussion of Isolation and Sequencing of cDNA Coding for Chymoelastase

One of the discoveries of the present invention is the first cloning of a gene from an entomopathogenic fungus and a description of aspects of its regulatory control. Sequencing of the Pr1 gene revealed that it is synthesized as a large precursor containing a signal peptide and a propeptide. The 18-amino acid signal sequence is atypical in the shortness of the hydrophobic core and its predicted α-helix secondary structure. The functional effects of these features in processing the protease through the endoplasmic reticulum remains to be explored. However, kinetic studies have demonstrated that the transit time between transcription of the 40.3 precursor and secretion of mature 28.6 kDA Pr1 is less than seven minutes; while the half-life of the precursor is considerably less (St. Leger et al., 1991). Consequently, the atypical features of the signal region must be conducive to rapid processing in Metarhizium. The pro-region is characteristic for proteases and is considered to mask the proteolytic activity of itself during transportation. Although the pro-regions of Pr1 and proteinase K do not share many highly conserved sequences, they are both predicted to possess extended regions of α-helix. Similar regions of α-helix are shown in the pro-region of the protease of S. cerevisiae but it is composed of much more hydrophyllic stretches of amino acids (Moehle et al., 1987). This suggests evolutionary pressure towards retention of secondary structure rather than of primary sequences.

Studies on the regulation of the Pr1 and Ssg. genes confirmed that the level of message is controlled by catabolite repression. Nuclear transcription assays support a role for regulation at the transcriptional level. However, the involvement of other factors, such as mRNA stabilizing and processing, is still possible. It has been demonstrated that nutrient levels regulate development of appressoria. Nutrient levels that allowed differentiation also derepressed the Pr1 gene in developing appressoria, indicating that nutrient levels coordinate regulation and expression of gene products required for both morphological development and enzymatic degradation of cuticular protein. Regulation by catabolite repression has been suggested for proteinase K because it is secreted when cultures of T album reach the stationary growth phase (Ebeling, W. et al, 1974 "Proteinase K from Tritirachium album Limber" Env. J. Biochem. 47, 91–97, incorporated herein by reference). If control by catabolite repression is confirmed for proteinase K, it would indicate that pathogenic specialization by M. anisopliae has not required major changes in protease regulation.

The biological role of subtilisin related proteases remains unknown, but it is likely that these enzymes function to scavenge extracellular proteins (Gunkel and Garren, 1989). Given that the proteinaceous insect cuticle will be a barrier to all fungi, then the ability of some saprophytes to produce a powerful extracellular protease may have pre-adapted them for entomopathogenicity. The similarities between proteinase K, the most active known serine endopeptidase (Bet), and Pr1 indicate that they separated in their evolutionary paths recently. A feature of Pr1 is its high isoelectric point (pI ca. 10) (St. Leger, R. J. et al, 1987c "Distribution of chymoelastases and trypsin-like enzymes in five species of entomopathogenic deutermycetes" Arch. Biochem, Biophys, 258, 123–131, incorporated herein by reference), compared with 8.9 for proteinase K (Ebeling et al, 1974). Net charge calculations of pI for Pr1 and proteinase K, based on amino acid sequences, were 8.55 and 8.06 respectively, but these calculations do not take into account any electrostatic interactions within the proteins. According to surface probability estimates (FIG. 11), Pr1 and proteinase K have net surface charges of +6 and +2 respectively. Under neutral and alkaline conditions, the surface of the Pr1 molecule would be positively charged. Previously, we demonstrated that electrostatic binding of Pr1 to the predominately negatively charged proteins in cuticle is a prerequisite for effective digestion of cuticle (St. Leger et al., 1986c, "Cuticle-degrading enzymes of entomopathogenic fungi: Mechanisms of interaction between pathogen enqymes and insect cuticle", J. Invertebr. Pathol. 47, 295–302, incorporated herein by reference.). Stronger binding due to the positively charged surface groups on Pr1 may therefore contribute to Pr1 showing a 33-fold higher activity as compared with proteinase K against insoluble cuticle proteins. These proteins contribute to the protein-protein and proteinchitin bonds which maintain the structural integrity of insect cuticles (Hepburn, H. R. 1985 "Structure of the integument" In: Comprehensive Insect Physiology, Biochemistry, and Pharmacology (3) (Kerkut, G. A. and Gilbert, L. I., eds.) Pergammon Press, Oxford pp. 1–58, incorporated herein by reference); the ability to rapidly solubilize structural proteins should assist penetration as well as providing nutrients for pathogen development.

Isolation of the Pr1 gene is an important step in the analysis of pathogenicity by *anisopliae*. Our results may also have widespread implications in the understanding of fungal entomopathogenecity as proteases similar to Metarhizium Pr1 in their active site serines and substrate specificities are produced by several species of entomopathogens during nutrient deprivation (St. Leger et al, 1987c). Likewise, cross-hybridizing bands with λPr1 indicated significant homologies between proteases of *M. anisopliae, A. Flavus* and *V. lecanii*. Most strains apparently harbored only one gene capable of hybridizing with λPr1. However, multiple protease genes exist in *V. lecnaii*, and it is conceiveable that they contribute to the *V. lecanii* protease isoenzyme family seen in iso-electric focusing gels (Charnley and St. Leger, 1991). Zoophthora (=Erynia) spp. produce cuticle degrading chymotrypsin activates very different in specificity to Metarhizium Pr1 (R. I. Samuels et al, 1990, "The partial characterization of endoproteases and exoproteases from three sepcies of entomopathogenic entomophthorales and two species of deuteromycetes", Mycopnathol, 110, 145–152). Likewise, *E. radicans* does not cross-hybridize with Pr1, indicating that proteases other than Pr1 type chymoelastases allow entomopathogenicity in some other systems.

Entomopathogenic strains have long been selected and improved using mutagenesis and selection as well as asexual genetic manipulations (Heale, 1989). Recombinant DNA methods offer a powerful set of additional techniques for strain improvement. Possible ways in which these techniques could be exploited are to increase gene copy number for increased production of enzymes or to clone the gene controlling the rate limiting step in the production of a toxin or other metabolite of interest. It may be possible to redirect formation of infection structures by modifying the triggers that initiate differentiation. An alternative approach is to transfer genes into non-pathogens with different hosts; for example, to equip a pathogen with the means of overcoming a particular host's defenses. The potential of this approach has been demonstrated with plant pathogens.

The art of adding genes to a fungal genome for studies on gene function has now become somewhat routine, apparently limited only by one's ability to manipulate the fungus. Recently, we adapted the protocols used for filamentous fungi to the transformation of *M. anisopliae*. Briefly: protoplasts, prepared by cell wall digestion, were stressed in the cold with $Ca^2$ and PEG-3000 in the presence of a plasmid which contained the benomyl resistance gene, benA3, from *Asperfillus nidulans* (M. S. Goettel et al, 1990, "Pathogenicity and growth of *Metarhizium anisopliae* stably transformed to benomyl resistance", Curr. Genet. 17, 129–132, incorporated herein by reference). Southern blot analysis revealed nonhomologous chromosomal integration. These transformants retained their pathogenicity to *Mandiica sexta* in the presence of benomyl, suggesting a strategy for the biocontrol of insects whereby transgenic strains could be used to control insect pests at the same time that fungicides were applied to control fungal pathogens of plants.

Having transformation technology available enables conclusive establishment of the role of a gene product in pathogenicity. Thus, it is possible to clone the genes for putative pathogenicity deteri-ninants and, after in vitro mutagenesis (deletions, insertions, or nucleotide substitutions within pre-determined sites within a DNA segment), reintroduce these genes into the wild-type organism. This would produce a near isogenic mutant strain with reduced pathogenesis depending on the importance of the gene. This technique consequently allows one to study gene activities in pathogens lacking a sexual stage, and is particularly useful where there is only one or two copies of the gene per genome, such as Pr1. With *M. anisopliae*, for example, it would be possible to interrupt the Pr1 gene by inserting the benA3 gene. Mutant fungi can then be analyzed for protease secretion and pathogenicity. It should also be possible to utilize new transformation procedures which do not depend on protoplast preparation including "blectroporation" and the "gene gun" which bombards cells with DNA-coated tungsten beads.

Other questions regarding fungal pathogenicity genes can also be answered by transformation. Thus, by transferring the Pr1 gene of *M. anisopliae* to *Aschersonia aleyrodis*, a poor protease producer which is limited in range to soft-bodied insects, one would determine whether the Pr1 gene can alter the range of pathogenicity in any given system. A further profitable direction for entomopathogens may lie in the study of their dazzling array of metabolites. To date, only the antibiotic and insect toxin Cordycepin (from *Cordyceps militaris*) and the actin-specific agent Cytochalasin C (from *M. anisopliae*) are commercially produced. Undoubtedly, many other novel compounds remain to be isolated with potential utility in medicine as well as pest control.

Aside from the more efficient use of fungal pathogens in pest control, a further long term goal is to engineer the genes for cuticle-degrading enzymes into vectors (viruses, bacteria, other fungi) or into plants. In order to digest the cuticle most effectively, a super vector(s) that elaborates the best anticuticle proteolytic, chitinolytic, and lipolytic enzymes might be constructed (Kramer et al., 1988). Pr1 is currently the best candidate for such a role in that it is the best characterized and most active known cuticle-degrading enzyme. Furthermore, as comparatively small differences in primary sequences (e.g. Pr1 vs. proteinase K) can substantially effect proteolytic efficiency, it should be possible to engineer proteases with modified activities. To this end, it will be necessary to obtain a more thorough knowledge of the parameters which influence proteolysis of cuticle.

While Pr1 has been previously isolated, chymoelastase can be purified and isolated from media hosting new organisms transformed for expression and secretion of chymoelastase. Heretofore, no use for a chymoelastase other than cuticle degradation has been proposed. The present invention teaches new uses for a chymoelastase, comprising, using the chymoelastase to selectively degrade protein in the presence of non-protein polymers. For example, chymoelastase could be used as an adjunct to an emulsifying agent. Because of its ability to degrade a broad array of protein substrates, chymoelastase would be excellent for removing proteinaceous stains. The addition of chymoelastase in fluid, semisolid, or gas transmission lines could aid in the clearing of proteinaceous masses blocking flow. This enzyme could be added to commercial products for degrading proteinaceous masses in plumbing lines (e.g. Liquid Plumber™).

Chymoelastase can also be used to selectively degrade tissue. Purified chymoelastase could be used to clarify wounds, by selectively placing isolated enzyme on damaged tissue. The enzyme would solublize the damaged tissue and could be controlled by the amount of application or by adding a specific inhibitor (e.g. turkey egg white) for chymoelastase after the desired amount of damaged tissue is removed. The patient would feel a slight itching sensation if the enzyme were to come into contact with healthy skin, but the enzyme is soluble in water and can be easily washed off. Along the same line, chymoelastase could be used to remove tissue from non-proteinaceous skeleton structure.

Furthermore, chymoelastase can be used to selectively degrade protein in the presence of one or more of the following substances: a) nucleic acids, b) carbohydrates, or c) lipids. This means it would be an excellent purifying agent for laboratory use.

The present invention includes the first genetically improved entomopathogenic fungus. Additional copies of the gene encoding the regulated cuticle-degrading *M. anisopliae* protease (Pr1) were inserted into the genome of *M. anisopliae* such that the gene was constitutively overexpressed. *Manduca sexta* larvae infected with the transformants became blackened as Pr1 produced in the haemocoel activated the prophenoloxidase system. The toxicity of Pr1 caused a 25% reduction in time of death and reduced food consumption by 45% compared to the wild-type fungus. An additional attractive feature of the system is that melanizing insects killed by the transformants were very poor substrates for fungal sporulation. This will reduce environmental persistence of the genetically engineered pathogen, thus providing biological containment.

Most entomopathogenic fungi, including *M. anisopliae*, infect insects by breaching the proteinaceous host cuticle. This is facilitated by the action of a subtilisin-like protease (designated Pr1) which solubilizes cuticle proteins assisting penetration and providing nutrients for further growth (St. Leger, R. J, Frank, D. C., Roberts, D. W. and Staples, R. C. Eur. J. Biochem. Pr1 production by *M. anisopliae* is under dual control of a general carbon catabolite repression/derepression mechanism and a carbon source (cuticle) specific induction mechanisms. As activation of fungal infection processes involves the induced expression of Pr1, constitutive over-expression of this gene is a direct strategy for engineering enhanced virulence.

Plasmid pMP4-Pt1 carries cDNA coding for the Pr1~protease of *M. anisopliae* cloned behind the constitutive *N. crassa* cross-pathway control (CPC) promoter in the pMP4 expression vector (obtained from Dr. M. Plamann, Texas A&M Univ.). To construct plasmid pBEN-Pr1, a 5.5 kb fragment of *M. anisopliae* DNA carrying Pr1 encoding a single transcript and including 1.5 kb upstream of it, was inserted in place of the pyr4 gene in the pBENA3 plasmid carrying the benomyl resistance gene benA3 from *Aspergillus nidulans*. Strains of *M. anisopliae* and *A. aleyrodis* were transformed directly with pBEN-Pr1 whereas strains were cotransformed with pMP4-Pr1 and pBENA3 (*M. anisopliae*) or pAN7-1 (*Aschersonia aleyrodis*) which contains the bacterial hygromycin phosphotransferase gene (fixed to ascomycete transcription signals).

We constructed pMAPR-1 which carries cDNA coding for the Pr1 protease cloned behind the constitutive *Aspergillus nidulans* glyceraldehyde-3-phosphate dehydrogenase (gpd) promoter. pMAPR-1 was constructed using standard procedures (Sambrook, J., Fritsch, E. F. and Maniatis, T. in Molecular Cloning a Laboratory Manual. second edition. Cold Spring Harbour laboratory Press. (1989), incorporated herein by reference.) The full-length cDNA for Pr1 in the Bluescript M13+vector was linearized, resected by digestion with BAL-31 nuclease, treated with DNA polymerase and ligated with the Nco1I digested blunt-ended pAN52-1 vector (obtained from Dr. Peter Punt of the TNO Medical Biology Laboratory, the Netherlands). Vector pAN52-1 carries the gpd promoter and the terminator region of the *A. nidulans* trp C gene joined at a Nco1 site (Punt, P. J., Oliver, R. P., Dingemance, M. D., Pouwels, P. H., and van den Hondel, C. A. M. J. J. Gene. 56:117–124, incorporated herein by reference.). Sequence analysis was used to confirm that the Pr1 initiator ATG is in frame with the gpd promoter. We grew the transformants under inducing conditions (shake cultures containing 1% cockroach cuticle (St. Leger, R. J, Frank, D. C., Roberts, D. W. and Staples, R. C. Eur. J. Biochem.) or in media containing 1% NAG (St. Leger, R. J., Durrands, P. K., Cooper, R. M. and Charnley, A. K. Arch. Microbiol. 150: 413–416 (1988), incorporated herein by reference.). Pr1 activity was assayed vs. Succinyl-(Alanyl) 2-Prolyl-Phenylalanine p-nitroanilide, 2 hrs after inoculation ($1\times10^7$ spores/100 ml culture media). Activities are expressed as $\mu$mol pNA $min^{-1}$ $ml^{-1}$. Production of Pr1 was confirmed by Western analysis with antisera to Pr1. The genomic structures of the recombinant fungi were confirmed by Southern hybridization of purified DNA. The DNA was digested with EcoRV, an enzyme that does not cut within pMAPR-1, to estimate copy numbers of the transforming plasmid in their genomes.

The expression cassette was introduced into *M. anisopliae* ARSEF 1080 [an American strain isolated from a Lepidopterous larva (*Heliothis zea*)] by cotransformation with the *Aspergillus nidulans* benomyl resistance plasmid pBENA3(Goettel, M. S., St. Leger, R. J., Bhairi, S., Jung, M. K., Oakley, B. R., Roberts, D. W. and Staples, R. C. Curr. Genet. 17: 129–132 (1990), incorporated herein by reference.). Transformants were selected for resistance to high levels (20 $\mu$g $ml^{-1}$) of benomyl and for constitutively expressed Pr1 by plating on nutrient-rich [nutrient agar (Difco) and 1% N-acetylglucosamine (NAG)] media incorporating insoluble elastin (0.08% w/v), a Pr1 substrate (St. Leger, R. J., Charnley, A. K. and Cooper, R. M. Arch. biochem. Biophys. 253: 221–232 (1987), incorporated herein by reference.). Four strains (con-Pr1-1 to 4) producing the largest elastin clearing zones were selected for production of single-spore cultures and retested for constitutive Pr1 production in shake flask cultures containing 1% NAG (Table 3). Detection of Pr1 in culture supernatants of NAG-containing media confirmed that processing and secretion of Pr1 can occur normally in a nutrient rich media which represses expression of Pr1 by wild type *M.*

*anisopliae*. All the recombinants showed wild-type levels of growth and conditation. Southern blot analysis revealed that copy numbers of Prl CDNA ranged from two to four (Table 3). The integration events seemed to be random (data not shown).

TABLE 3

*Metarhizium anisopliae* wild type and transformants chosen for analysis

| | Approximate | Expression of Prl in cockroach cuticle media | Expression of Prl in 1% NAG media |
|---|---|---|---|
| Wild | — | 0.22 ± 0.03 | 0 |
| Trans-formant | | | |
| T. con. Prl-1 | 2 | 0.28 ± 0.03 | 0.08 ± 0.02 |
| T. con. Prl-2 | 3 | 0.30 ± 0.04 | 0.11 ± 0.03 |
| T. con. Prl-3 | 3 | 0.35 ± 0.03 | 0.14 ± 0.03 |
| T. con. Prl-4 | 4 | 0.38 ± 0.04 | 0.17 ± 0.03 |

The biological activity of the recombinants was assessed by inoculating 5th instar *M. sexta* larvae with an $LC_{100}$ dose ($5 \times 10^6$ conidia). Infection with recombinant strains caused partial hydrolysis of haemolymph proteins and extensive melanization in the body cavity. These insects contained sufficient amounts of Prl in the haemolymph to be detected by Western blot analysis indicating that transgenic strains continued to produce Prl in the haemocoel of caterpillars following penetration of the cuticle. By contrast, infection of larvae with wild type did not alter the profile of haemolymph proteins and larvae remained green. When Prl, purified from cuticle culture media by iso-electric focusing and affinity chromatography,(St. Leger, R. J., Charnley, A. K. and Cooper, R. M. Arch. biochem. Biophys. 253: 221–232 (1987), incorporated herein by reference.) was injected into 5th instar larvae of gypsy moth (*Lymantria dispar*) or *M. sexta* (100 ng per larva), the caterpillars blackened and died within 30 min.

We also demonstrated that *A. aleyrodis* can be used for expression of heterologous proteins by introducing the Prl gene. *A. aleyrodis* produces low levels of endogenous protease and is only pathogenic to soft-bodied insects (St. Leger et al., 1987a). The amino-terminus of the *A. aleyrodis*-produced *M. anisopliae* proteinase was heterogeneous, consisting of two forms; one with the same Ntermiinus as *M. anisopliae*-produced Pr1 Gly-Ile-Thr-Glu-Glu-Ser, and the other having Thr-Glu-Glu-Ser. The susceptibility of second, third, and fourth instar larvae on leaf discs was assayed using an immersion technique. Infection levels of young whiteflies (normal host) was similar (ca. 85%) for both wild type and strains constitutively expressing Pr1. Infection levels of nearly mature (heavy cuticle) whiteflies were 6% (wild type) and 41% (transformed) indicating that some of the limitations of this pathogen can be overcome by the acquisition of a functioning protease gene. These results provide the first conclusive demonstration of the utility of heterologous gene expression in molecular analysis of the insect-fungal interaction, and for strain construction of improved mycoinsecticides.

The addition of 20 ng of Pr1 to 0.3 ml of *M. sexta* haemolymph caused a rapid (<5 min) melanization. The presence of leupeptin (5 $\mu$g), an inhibitor of trypsins with no effect on Pr1, (St. Leger, R. J., Charnley, A. K. and Cooper, R. M. Arch. biochem. Biophys. 253: 221–232 (1987), incorporated herein by reference.) inhibits prophenoloxidase activation by Pr1 indicating that Pr1 most likely acts indirectly by activating an earlier stage in a cascade terminating in prophenoloxidase activation.

Constitutive expression of Pr1 speeds up the disease process and improves insecticidal activity of the recombinants as demonstrated by reductions of about 30 h in median survival time, a decrease of 25% compared to wild type (Table 4). Microscopic examination and quantitative culturing (serial dilution plate counts (St. Leger, R. J., Durrands, P. K., Charnley, A. K., and Cooper, R. M. J. Invertebr Pathol. 52: 285–293 (1988), incorporated herein by reference.)) revealed that hyphal bodies (blastospores and short hyphal lengths) of the wild type strain proliferated within the haemolymph ($2.3\times10^6\pm4\times10^5$ colony forming units per ml, n=10, 110 hrs after inoculation) prior to death ($LT_{50}$=120 $h^{-1}$). By contrast, relatively few propagules ($7.8\times10^4\pm7\times10^3$, n=10, 85 hrs after inoculation) were present in con-Pr1-4 infected insects consistent with the early mortalities ($LT_{50}$=93 $h^{-1}$) being caused by toxicosis (Samuels, R. I., Charnley, A. K., and Reynolds, S. E. Mycopathologia. 104:51–58 (1988), incorporated herein by reference.). The median lethal dose ($LC_{50}$) values for wild type and transformants were not significantly different indicating that efficiency of infection (attachment and penetration) is not effected by constitutive over-expression of Pr1. Constitutive over-expression of Pr1 is unlikely to alter host range. Specificity is usually controlled by infection events at the level of the cuticle (St. Leger, R. J, Frank, D. C., Roberts, D. W. and Staples, R. C. Eur. J. Biochem. which would be unaltered by the continuance of Pr1 production after cuticle penetration. Consistent with this, transformants resembled the parent strain in being pathogenic to gypsy moth larvae at massive doses only ($LC_{50}>10^8$ spores $ml^{-1}$), and not displaying pathogenicity to beetle larvae (*Tenebrio molitor*) at $10^9$ spores $ml^{-1}$. We measured the weight of food consumed to determine whether infection of *M.sexta* with con-Pr1-4 could reduce feeding, the critical commercial parameter of pesticides. In several experiments, insects infected with con-Pr1-4 consistently ate 40–45% less diet compared to individuals infected with wild type.

TABLE 4

Dose-mortality response of larval *Manduca sexta*[a] infected with wild-type (wt.) or recombinant fungus.

| | LC50 conidia ml − 1g−1 (95% fiducial limit) | Slope | LT50 h−1 (95% fiducial limit) | Slope |
|---|---|---|---|---|
| wt | $3.14\times10^5$ ($2.03 - 5.54\times10^5$) | 1.87 | 128 (120–136) | 17.2 |
| T-Con-Prl-3 | $2.98\times10^5$ ($1.85 - 5.50\times10^5$) | 2.15 | 96 (92–106) | 12.3 |
| T-Con-Prl-4 | $2.75\times10^5$ ($1.81 - 5.32\times10^5$) | 2.21 | 93 (88–102) | 11.7 |

[a]Ten newly emerged 5th instar larvae (mean wt. 1.4 ± 0.13 g) per dose were inoculated by dipping into conidial suspensions and transferred to containers with artificial diet at 25° C., 70% RH to follow the course of the infection (St. Leger, R. J., Durrands, P. K.,, Charnley, A. K., and Cooper, R. M. J. Invertebr Pathol. 52: 285–293 (1988), incorporated herein by reference.). LC50 = the spore concentration that gave 50% mortality within 7 days. LT50 = the time after inoculation when 50% of the larvae have died.

The development of genetically enhanced mycoinsecticides clearly offers an alternative to chemical pesticides. An additional attractive feature of our system is that blackened insects killed by transgenic strains were very poor substrates for fungal growth and sporulation. Failure to sporulate is very attractive from both a commercial and an environmental standpoint as it would presumably lead to the eventual extinction of transformants, reducing environmental impact and allowing repeat sales. Furthermore, the development of strains of *M. anisopliae* that constitutively express Pr1 provides an example of a strategy which, in using a homologous gene, is less likely to raise public concern. Combined with the reduced survival time and feeding of infected insects, this makes the modified fungi a realistic candidate for a biological insecticide.

The protease provides a novel reagent for the pesticidal arsenal including a unique mode of action (activation of prophenoloxidase) for combating resistance or selected pests when expressed in an appropriate fungal or insectivorous viral vector. Up until now, fungal genes have played little part in the implementation of biotechnology in crop protection which is surprising given both the dazzling array of metabolites they produce and that lack of useful pesticidal genes for transfer has been a major constraint on the development of this technology (Gatehouse, A. M. R., Boulter, D., and Hilder, V. A. in Plant Genetic Manipulation for Crop Protection. (eds Gatehouse, A. M. R., Hilder, V. A., and Boulter, D.) 155–182. (CAB International), 1992, incorporated herein by reference.). The present invention demonstrates that it is possible to isolate fungal genes for proteins with fast-acting insecticidal activity.

Producing an engineered biocontrol fungus may not always be the most effective means of delivering a fungal anti-insect gene (depending on the insect pest and host plant in question). The potential of using baculoviruses for insect pest control has long been recognized as they have minimal environmental impact and high target specificity. An important goal of genetically engineering these viruses has been to overcome their inability to kill target insects rapidly. An example of this type of approach has been the construction of improved baculovirus insecticides containing toxin genes from spiders or mites (Stewart et al, 1991). Several groups are also investigating the potential of insect hormones or hormone regulators, but with little success so far at improving pathogen performance (e.g., Hammock et al., 1990). Based on the potential utility of foreign gene inserts constructed to date, particularly toxins, the search for additional pesticidal genes is clearly a commercial priority. The insertion and expression of additional genes is performed very simply. The primary limitation in this area has been the availability of pesticidal genes (Wood, 1994).

Presently, baculoviruses compete inadequately with classical insecticides partly because of their slow speed of action. Viruses can be engineered to express Pr1 which would enhance their speed of killing. The Pr1 protease provides a novel reagent for the pesticidal arsenal including a unique mode of action (activation of prophenoloxidase) for combating resistance or selected pests when expressed in an appropriate fungal or insectivorous viral vector. We have found that 50 ng of Pr1 will kill a fifth instar gypsy moth larvae within 15 min. of injection; a process associated with melanization throughout the body cavity. The melanin cascade reaction is specific to insects. Therefore Pr1 is a special "bullet" that is extremely toxic to insects but relatively safe for other types of organisms. The speed and specificity of the toxic effects of the Pr1 enzyme make it an excellant choice for use in insect control agents.

Analysis of the Pr1 cDNA sequence has shown that the protease is synthesized as a precursor, a biologically inactive form (St. Leger et al., 1992c). The pro-region of the protease masks the proteolytic activity of the enzyme during passage through the cell and undergoes cleavage at the cell membrane. We wish to express the precursor of Pr1 rather than the mature form because precursor regions of other proteases participate in the correct folding of the protein necessary to produce a functional molecule (e.g. Silen et al., 1989). Furthermore, if the mature peptide was produced in the cell it might prematurely interupt cellular processes required for efficient viral infection. Along these lines, the Pr1 gene would preferably be placed behind a "late promoter" such that the enzyme was produced after signifigant viral replication within the cell.

Complex processes required to produce eukaryotic proteins such as post-translational proteolytic cleavage are frequently reported in BEVs (O'Rielly et al, 1992). However, several studies have found that proteinases initially accumulate as the precursor in Sf cells infected with recombinant baculoviruses. The precursors are converted at later stages of infection to active enzyme by unknown cellular factors (e.g. Vernet et al., 1990; McMaster et al., 1994). Viral proteinases facilitate the lytic release of AcM-NPV virions from infected cells (Slack, 1994; Dougherty and Semler, 1993). These proteinases are also expressed as pro-proteases at late times in AcMPNV infection coincident with expression of the polyhedrin gene promoter (Slack, 1994). The proteinase papain was reported to be secreted in an active form when expressed in Sf cell cultures by an AcMNPV expression vector (Vernet et al., 1990) but secretion was measured $\geq 48$ h and therefore papain was likely released after virus-induced lysis of infected cells.

Protection of crops from their insect pests is already a major goal of plant genetic engineering. Fungal genes with anti-insect activity could be used in plant transformation procedures so the insect will be forced to encounter the gene product when feeding or interacting with the specific host plant. Thus, specific crops and fields are targeted without the danger of spread of a genetically engineered fungal pathogen outside of the specific field/crop to other, possibly beneficial, insect populations. Many of the natural defense mechanisms in plants involve interactions of numerous gene products in complex, multistep metabolic pathways which are more difficult to manipulate than the introduction of a single new gene (Hilder et al, 1992). By contrast, many of the pathogenicity traits described in microbes, including fungi, are regulated by single genes; hence, genetic manipulation offers attractive possibilities for enhancing host resistance.

To date, the vast majority of the work on incorporation of microbial genes, as well as all other aspects of microbially mediated biocontrol, centers around *Bacillus thuringiensis* toxins (Feitelson et al., 1992). As a result of relying on a single agent for biocontrol, there is mounting concern that the evolution of resistance to Bt toxin will greatly reduce its utility (Tabashnik, 1994). Also, Bt toxin genes have to be re-engineered to eliminate AT-rich regions to permit sufficient expression in plant cells (Adang et al., 1993). This may limit the range of toxin genes usefully expressed in plants. By contrast, Pr1 lacks ATTTA instability elements. We have shown that Pr1 is a mild antifeedant,toxic by ingestion and degrades peritrophic membranes of *T. ni* at basic pH. When making transgenci plants, the Pr1 gene could be placed behind a promoter related to responds to a wound such that the gene would only be expressed when the plant was being eaten.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A recombinant virus, microorganism, cell, plant, or fungus, wherein said recombinant virus, microorganism, cell or fungi is the product of an insertion of a gene expression vector including a DNA sequence that encodes a chymoelastase enzyme, protein Pr1, which as translated from the appropriate mRNA sequence is the amino acid sequence found in SEQ ID NO: 2, which after cleavage of the signal sequence and propeptide has the enzymatic and biologic activity of the cuticle-degrading chymoelastase produced by the entomopathogenic fungus *Metarhizium anisopliae*, into a host such that said recombinant virus, microorganism, cell, plant or fingus host is capable of expressing said protein Pr1 amino acid sequence found in said SEQ ID NO: 2.

2. The fungus of claim 1 wherein said host is *Metarhizium anisopliae* wherein said Pr1 expression is induced without nutrient deprivation.

3. An insecticide comprising a virus, microorganism, cell or fungus of claim 1.

4. The insecticide of claim 3 wherein when said virus, microorganism, cell or fungus infects, is eaten by, or otherwise taken up by an insect, said virus, microorganism, cell or fungus is capable of expressing the enzymatically active form of said Pr1 protein, that has the enzymatic and biologic activity of the cuticle-degrading protease, chymoelastase, produced by the entomopathogenic fungus *Metarhizium anisopliae* within said insect such that Pr1 activates a prophenoloxidase system within said insect.

5. The virus, microorganism, cell or fungus host of claim 1 wherein the amino acid sequence of SEQ. ID. NO. 2 can undergo cleavage of the signal sequence and propeptide so as to have the enzymatic and biologic activity of the cuticle-degrading chymoelastase produced by the entomopathogenic fungus *Metarhizum anisopliae.*

6. A purified and isolated recombinant DNA molecule comprising a cDNA sequence which codes for a protein, Pr1, derived from *Metarhizium anisopliae*, as shown in Sequence I.D. No. 2.

7. A method of using the DNA molecule of claim 6, comprising the step of translating said DNA molecule into a Pr1 protein such that said Pr1 protein is appropriately modified to yield the amino acid sequence as shown in Sequence I.D. No. 2 so as to produce a protease with the enzymatic and biologic activity of the cuticle-degrading chymoelastase Pr1.

8. A plasmid vector containing the cDNA molecule of claim 6 which was deposited as NRRL B-18853.

9. A method of using the DNA molecule of claim 6, comprising the step of translating said DNA molecule into a Pr1 protein such that said Pr1 protein is appropriately modified so that said Pr1 protein can be used to degrade protein in the presence of non-protein polymers wherein said protein is degraded and said non-protein polymers are not degraded.

10. The method of claim 8, wherein said Pr1 protein is used in one of the following ways selected from the group consisting of:

a) as an adjunct to an emulsifying agent;

b) to selectively degrade tissue;

c) to clarify wounds by solubilizing dead tissue;

d) to remove tissue from non-proteinaceous skeletal structure;

e) to remove proteinaceous stains;

f) to degrade proteinaceous masses in fluid, semisolid, or gas transmission lines; and g) to degrade proteins in the presence of one or more of the following substances selected from the group consisting of: 1) nucleic acids, 2) carbohydrates, and 3) lipids.

11. A method of obtaining a DNA molecule, from an entomopathogenic fungus, which codes for a chymoelastase, comprising:

a) inducing, through the use of nutrient deprivation, a culture isolated from an entomopathogenic fungus capable of producing a chymoelastase to express a chymoelastase;

b) isolating mRNA from said culture;

c) preparing a cDNA library from said isolated mRNA; and d) differentially screening said cDNA library by using cDNA probes derived from rapidly glowing mycelia and nutrient deprived mycelia, and screening for cDNA molecules coding for said chymoelastase.

12. A purified and isolated translatable mRNA molecule that encodes the Pr1 amino acid sequence, as shown in Sequence I.D. NO. 2.

13. A plant which is the product of an insertion of a gene expression vector including a DNA sequence that encodes a chymoelastase enzyme, protein Pr1, which as translated from the appropriate mRNA sequence is the amino acid sequence found in SEQ ID NO: 2, which after cleavage of the signal sequence and propeptide has the enzymatic and biologic activity of the cuticle-degrading chymoelastase produced by the entomopathogenic fungus *Metarhizium anisopliae*, into a host such that said plant host is capable of expressing said protein Pr1 amino acid sequence as encoded by said SEQ ID NO: 2.

14. A method of obtaining a cDNA molecule, from an entomopathogenic fungus, which codes for a chymoelastase, comprising:

a) inducing, through the use of nutrient deprivation, an entomopathogenic fungus culture that is capable of producing a chymoelastase to express a chymoelastase;

b) isolating mRNA from said culture;

c) preparing a cDNA library from said isolated mRNA; and d) screening by homology said cDNA library by using cDNA probes whose sequences encode for at least a portion of their length a conserved consensus sequence based on an alignment of Pr1 and at least one subtilisin-like protease, and identifying cDNA molecules coding for said chymoelastase.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1545 base pairs
      (B) TYPE: nucleic acid
      (C) STRANDEDNESS: double
      (D) TOPOLOGY: linear (ii) MOLECULE TYPE: cDNA to mRNA (vi) ORIGINAL SOURCE:
      (A) ORGANISM: Metarhizium anisopliae (vii) IMMEDIATE SOURCE:
      (A) LIBRARY: genomic
      (B) CLONE: lambda GT10

(ix) FEATURE:
      (A) NAME/KEY: mat_peptide
      (B) LOCATION: 83..1243

(ix) FEATURE:
      (A) NAME/KEY: CDS
      (B) LOCATION: 80..1243

(xi) SEQUENCE DESCRIPTION: SEQ ID NO:1:

```
CGCGGCCGCA TTCCATCAAA TCAACCTCGG TTTCTGCCCA ACATCTCTGG TCTTTGGTCC        60

CGTACTAGAA TTTGCAATC ATG CAT CTG TCT GCT CTT CTC ACT CTT CTC CCA       112
                     Met His Leu Ser Ala Leu Leu Thr Leu Leu Pro
                      -1   1               5                  10

GCC GTT CTG GCT GCC CCT GCC ACT ATT GGC CGG CGC GCT GAG CCA GCT        160
Ala Val Leu Ala Ala Pro Ala Thr Ile Gly Arg Arg Ala Glu Pro Ala
                 15                  20                  25

CCT CTC TTC ACT CCT CAG GCT GAG AGC ATC ATT GCC GAC AAG TAT ATT        208
Pro Leu Phe Thr Pro Gln Ala Glu Ser Ile Ile Ala Asp Lys Tyr Ile
         30                  35                  40

GTC AAG TTC AAG GAT GAT ATT GCC CGT ATC GCT ACC GAT GAT ACG GTG        256
Val Lys Phe Lys Asp Asp Ile Ala Arg Ile Ala Thr Asp Asp Thr Val
     45                  50                  55

AGC GCT CTT ACC TCC AAA GCC GAC TTC GTT TAC GAG CAC GCC TTC CAT        304
Ser Ala Leu Thr Ser Lys Ala Asp Phe Val Tyr Glu His Ala Phe His
 60                  65                  70

GGG TTT GCA GGC TCC CTC ACC AAG GAG GAG CTG AAG ATG CTT CGT GAG        352
Gly Phe Ala Gly Ser Leu Thr Lys Glu Glu Leu Lys Met Leu Arg Glu
 75                  80                  85                  90

CAC CCC GGT GTC GAT TTC ATT GAG AAG GAC GCT GTG ATG CGT ATC AGC        400
His Pro Gly Val Asp Phe Ile Glu Lys Asp Ala Val Met Arg Ile Ser
             95                  100                 105

GGC ATC ACT GAG CAG AGC GGT GCT CCC TGG GGT CTT GGG CGC ATC TCT        448
Gly Ile Thr Glu Gln Ser Gly Ala Pro Trp Gly Leu Gly Arg Ile Ser
         110                 115                 120

CAC CGC AGT AAG GGA AGC ACC ACC TAT CGC TAC GAT GAT AGT GCT GGT        496
His Arg Ser Lys Gly Ser Thr Thr Tyr Arg Tyr Asp Asp Ser Ala Gly
     125                 130                 135

CAG GGT ACT TGC GTA TAT ATC ATT GAC ACT GGT ATT GAG GCC TCC CAC        544
Gln Gly Thr Cys Val Tyr Ile Ile Asp Thr Gly Ile Glu Ala Ser His
 140                 145                 150

CCC GAG TTT GAG GGT CGC GCC ACT TTT CTT AAG AGC TTC ATC AGC GGT        592
Pro Glu Phe Glu Gly Arg Ala Thr Phe Leu Lys Ser Phe Ile Ser Gly
155                 160                 165                 170
```

```
CAA AAC ACT GAT GGC CAC GGC CAT GGG ACT CAC TGC GCT GGT ACC ATT        640
Gln Asn Thr Asp Gly His Gly His Gly Thr His Cys Ala Gly Thr Ile
                175                 180                 185

GGT AGC AAG ACC TAC GGT GTT GCC AAA AAG GCT AAG CTC TAT GGT GTC        688
Gly Ser Lys Thr Tyr Gly Val Ala Lys Lys Ala Lys Leu Tyr Gly Val
                190                 195                 200

AAG GTT CTT GAC AAC CAG GGC AGT GGT TCC TAC TCC GGT ATC ATC AGT        736
Lys Val Leu Asp Asn Gln Gly Ser Gly Ser Tyr Ser Gly Ile Ile Ser
                205                 210                 215

GGC ATG GAC TAC GTT GCA CAG GAC TCC AAG ACC CGC GGC TGC CCC AAC        784
Gly Met Asp Tyr Val Ala Gln Asp Ser Lys Thr Arg Gly Cys Pro Asn
            220                 225                 230

GGC GCC ATT GCT TCC ATG AGC CTG GGA GGT GGC TAC TCG GCG TCC GTC        832
Gly Ala Ile Ala Ser Met Ser Leu Gly Gly Gly Tyr Ser Ala Ser Val
235                 240                 245                 250

AAC CAA GGT GCT GCT GCT TTG GTC AAT TCT GGT GTC TTC CTT GCC GTC        880
Asn Gln Gly Ala Ala Ala Leu Val Asn Ser Gly Val Phe Leu Ala Val
                255                 260                 265

GCC GCT GGC AAC GAT AAC CGG GAT GCC CAG AAC ACC TCT CCC GCT TCC        928
Ala Ala Gly Asn Asp Asn Arg Asp Ala Gln Asn Thr Ser Pro Ala Ser
                270                 275                 280

GAG CCT TCT GCC TGC ACT GTT GGT GCC TCT GCG GAA AAT GAC AGC CGA        976
Glu Pro Ser Ala Cys Thr Val Gly Ala Ser Ala Glu Asn Asp Ser Arg
                285                 290                 295

TCT TCC TTC TCC AAC TAC GGC AGA GTT GTC GAT ATT TTC GCT CCT GGT       1024
Ser Ser Phe Ser Asn Tyr Gly Arg Val Val Asp Ile Phe Ala Pro Gly
                300                 305                 310

AGC AAT GTT CTT TCC ACC TGG ATT GTT GGC CGC ACA AAC TCC ATC TCT       1072
Ser Asn Val Leu Ser Thr Trp Ile Val Gly Arg Thr Asn Ser Ile Ser
315                 320                 325                 330

GGT ACC TCC ATG GCT ACT CCC CAT ATT GCC GGT CTG GCT GCC TAC CTC       1120
Gly Thr Ser Met Ala Thr Pro His Ile Ala Gly Leu Ala Ala Tyr Leu
                335                 340                 345

AGT GCG CTC CAA GGC AAG ACT ACC CCT GCC GCT CTT TGC AAG AAG ATC       1168
Ser Ala Leu Gln Gly Lys Thr Thr Pro Ala Ala Leu Cys Lys Lys Ile
                350                 355                 360

CAG GAC ACT GCT ACC AAG AAC GTG CTC ACC GGT GTT CCC TCT GGC ACT       1216
Gln Asp Thr Ala Thr Lys Asn Val Leu Thr Gly Val Pro Ser Gly Thr
                365                 370                 375

GTC AAC TAC CTT GCC TAC AAC GGT GCC TAAATTCTTA ACTTGAGCAA             1263
Val Asn Tyr Leu Ala Tyr Asn Gly Ala
                380                 385

GGGGGGGAAC CCTTCAGTGA AGAGACGGCG ATTGGTTGGT TGTATATTTG AGATAATTTC     1323

CAACGCTCGA ATCCCCCCCA AAGGTATATA TTTATATTTC TATATTTTCT TCACCCAGTA     1383

CATTATGATG ATGGAACATG ACCTTTCCCA ATATAAGATG TCTTTGCAGC AGAAGGAAAT     1443

GAAGATGTTA TCGGGCGTGT AGCTCAGAGT GCAGAAGTTG AGCTACTAGG GAATAAATCT     1503

AGGAGAGTTT ATGGCCAAAA AAAAAAAAAA AAAGCGGCCG CG                       1545

(2) INFORMATION FOR SEQ ID NO:2:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO:2:

Met His Leu Ser Ala Leu Leu Thr Leu Leu Pro Ala Val Leu Ala Ala
```

-continued

```
  -1   1                  5                      10                        15
 Pro Ala Thr Ile Gly Arg Arg Ala Glu Pro Ala Pro Leu Phe Thr Pro
                     20                  25                      30

Gln Ala Glu Ser Ile Ile Ala Asp Lys Tyr Ile Val Lys Phe Lys Asp
                     35                  40                      45

Asp Ile Ala Arg Ile Ala Thr Asp Asp Thr Val Ser Ala Leu Thr Ser
             50                      55                  60

Lys Ala Asp Phe Val Tyr Glu His Ala Phe His Gly Phe Ala Gly Ser
             65                      70                  75

Leu Thr Lys Glu Glu Leu Lys Met Leu Arg Glu His Pro Gly Val Asp
     80                      85                  90                      95

Phe Ile Glu Lys Asp Ala Val Met Arg Ile Ser Gly Ile Thr Glu Gln
                     100                 105                     110

Ser Gly Ala Pro Trp Gly Leu Gly Arg Ile Ser His Arg Ser Lys Gly
                     115                 120                     125

Ser Thr Thr Tyr Arg Tyr Asp Asp Ser Ala Gly Gln Gly Thr Cys Val
                 130                     135                 140

Tyr Ile Ile Asp Thr Gly Ile Glu Ala Ser His Pro Glu Phe Glu Gly
         145                     150                     155

Arg Ala Thr Phe Leu Lys Ser Phe Ile Ser Gly Gln Asn Thr Asp Gly
 160                     165                     170                 175

His Gly His Gly Thr His Cys Ala Gly Thr Ile Gly Ser Lys Thr Tyr
                     180                     185                 190

Gly Val Ala Lys Lys Ala Lys Leu Tyr Gly Val Lys Val Leu Asp Asn
                 195                     200                 205

Gln Gly Ser Gly Ser Tyr Ser Gly Ile Ile Ser Gly Met Asp Tyr Val
                 210                     215                 220

Ala Gln Asp Ser Lys Thr Arg Gly Cys Pro Asn Gly Ala Ile Ala Ser
                 225                     230                 235

Met Ser Leu Gly Gly Gly Tyr Ser Ala Ser Val Asn Gln Gly Ala Ala
 240                     245                     250                 255

Ala Leu Val Asn Ser Gly Val Phe Leu Ala Val Ala Ala Gly Asn Asp
                     260                     265                 270

Asn Arg Asp Ala Gln Asn Thr Ser Pro Ala Ser Glu Pro Ser Ala Cys
                 275                     280                     285

Thr Val Gly Ala Ser Ala Glu Asn Asp Ser Arg Ser Ser Phe Ser Asn
                 290                     295                     300

Tyr Gly Arg Val Val Asp Ile Phe Ala Pro Gly Ser Asn Val Leu Ser
             305                     310                     315

Thr Trp Ile Val Gly Arg Thr Asn Ser Ile Ser Gly Thr Ser Met Ala
 320                     325                     330                 335

Thr Pro His Ile Ala Gly Leu Ala Ala Tyr Leu Ser Ala Leu Gln Gly
                     340                     345                 350

Lys Thr Thr Pro Ala Ala Leu Cys Lys Lys Ile Gln Asp Thr Ala Thr
                 355                     360                     365

Lys Asn Val Leu Thr Gly Val Pro Ser Gly Thr Val Asn Tyr Leu Ala
             370                     375                     380

Tyr Asn Gly Ala
         385
```